(12) United States Patent
Zygorodimos et al.

(10) Patent No.: US 12,220,582 B2
(45) Date of Patent: Feb. 11, 2025

(54) ASSESSING RESPONSES TO SENSORY EVENTS AND PERFORMING TREATMENT ACTIONS BASED THEREON

(71) Applicant: Cochlear Limited, Macquarie University (AU)

(72) Inventors: Matthew Zygorodimos, Macquarie University (AU); James Davies, Macquarie University (AU); Rishi Wadhwani, North Ryde (AU)

(73) Assignee: Cochlear Limited, Macquarie University (AU)

( * ) Notice: Subject to any disclaimer, the term of this patent is extended or adjusted under 35 U.S.C. 154(b) by 742 days.

(21) Appl. No.: 17/413,741

(22) PCT Filed: Jun. 15, 2020

(86) PCT No.: PCT/IB2020/000477
§ 371 (c)(1),
(2) Date: Jun. 14, 2021

(87) PCT Pub. No.: WO2020/260942
PCT Pub. Date: Dec. 30, 2020

(65) Prior Publication Data
US 2022/0054842 A1    Feb. 24, 2022

Related U.S. Application Data

(60) Provisional application No. 62/866,127, filed on Jun. 25, 2019.

(51) Int. Cl.
*A61N 1/36* (2006.01)
*A61N 1/05* (2006.01)
(Continued)

(52) U.S. Cl.
CPC ....... *A61N 1/36139* (2013.01); *A61N 1/0541* (2013.01); *A61N 1/36038* (2017.08);
(Continued)

(58) Field of Classification Search
CPC .. A61N 1/0541; A61N 1/36038; G10L 25/78; H04R 25/606; H04R 2225/41; H04R 2225/55; H04R 2225/67; H04R 2460/13
See application file for complete search history.

(56) References Cited

U.S. PATENT DOCUMENTS 5,824,022 A    10/1998    Zilberman et al.
8,996,120 B1   3/2015     Calle et al.
(Continued)

FOREIGN PATENT DOCUMENTS

| CN | 107548563 A | 1/2018 |
|---|---|---|
| CN | 113490524 A | 10/2021 |
| KR | 10-2015-0111157 A | 10/2015 |

OTHER PUBLICATIONS

International Search Report and Written Opinion in counterpart International Application No. PCT/US2020/000477, mailed Nov. 5, 2020, 9 pages.

*Primary Examiner* — Paula J Stice
(74) *Attorney, Agent, or Firm* — Edell, Shapiro & Finnan, LLC

(57) ABSTRACT

Examples disclosed herein are relevant to monitoring and treating sensory conditions affecting an individual. Sensors and intelligence integrated within a sensory prosthesis (e.g., an auditory prosthesis) can automatically obtain objective data regarding the ability of one or more of an individuals senses during day-to-day activities. A treatment action can be taken based on the objective data. Further disclosed herein are techniques relating to reducing the gathering of (Continued)

irrelevant sensory input and automatically transmitting relevant data to a caregiver device.

25 Claims, 13 Drawing Sheets

(51) Int. Cl.
    *A61N 1/372*     (2006.01)
    *G10L 25/51*     (2013.01)
    *G10L 25/78*     (2013.01)
    *G16H 20/40*     (2018.01)
    *H04R 25/00*     (2006.01)

(52) U.S. Cl.
    CPC .......... *A61N 1/37252* (2013.01); *G10L 25/51* (2013.01); *G10L 25/78* (2013.01); *G16H 20/40* (2018.01); *H04R 25/505* (2013.01); *H04R 25/554* (2013.01); *H04R 25/606* (2013.01); *A61N 1/36046* (2013.01); *H04R 2225/41* (2013.01); *H04R 2225/55* (2013.01); *H04R 2225/67* (2013.01); *H04R 2460/07* (2013.01); *H04R 2460/13* (2013.01)

(56) References Cited

U.S. PATENT DOCUMENTS

| | | | |
|---|---|---|---|
| 9,967,681 | B2 | 5/2018 | Oplinger et al. |
| 10,198,964 | B2 | 2/2019 | Reed et al. |
| 2013/0308802 | A1 | 11/2013 | Eaton et al. |
| 2014/0336448 | A1 | 11/2014 | Banna et al. |
| 2016/0030744 | A1 | 2/2016 | Hubert-Brierre |
| 2017/0280253 | A1 | 9/2017 | Oplinger et al. |
| 2018/0125415 | A1 | 5/2018 | Reed et al. |
| 2019/0090073 | A1* | 3/2019 | Wendt .................. A61B 5/125 |

* cited by examiner

ASSESSING RESPONSES TO SENSORY EVENTS AND PERFORMING TREATMENT ACTIONS BASED THEREON

This application is being filed on Jun. 15, 2020, as a PCT International Patent application and claims the benefit of priority to U.S. Provisional patent application Ser. No. 62/866,127, filed Jun. 25, 2019, the entire disclosure of which is incorporated by reference in its entirety.

CROSS-REFERENCE TO RELATED APPLICATIONS

This application is related to, but does not claim the benefit of priority to: U.S. Provisional Patent Application No. 62/750,394, titled "Passive Fitting Techniques"; U.S. Provisional Patent Application No. 62/703,373, titled "Habilitation and/or rehabilitation methods and systems"; and U.S. Provisional Patent Application No. 62/862,181, titled "Improving Musical Perception of a Recipient of an Auditory Device". These related applications are incorporated by reference herein in their entireties for any and all purposes.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In an example, there is an auditory prosthesis apparatus comprising: an implantable or wearable housing; a stimulator at least partially disposed within the housing and configured to impart energy to tissue of a recipient of the auditory prosthesis apparatus to evoke a hearing percept in the recipient; a plurality of sensors; and a processor configured to perform operations. The operations include: receiving event sensor data from the plurality of sensors; detecting an occurrence of an auditory event proximate the auditory prosthesis apparatus using the event sensor data; detecting a response by the recipient to the occurrence of the auditory event using response sensor data; characterizing the response by the recipient using the response sensor data; and taking a treatment action relating to the recipient based on characterizing the response.

In an example, the plurality of sensors include a microphone. In an example, detecting the occurrence includes: receiving an audio signal from the microphone; determining whether the audio signal includes speech asking a question; and responsive to determining that the audio signal includes speech asking a question, determine that an auditory event proximate the auditory prosthesis occurred. In an example, detecting the response by the recipient includes detecting a speech response by the recipient. In an example, characterizing the response by the recipient includes: determining a length of time taken from the question being asked to the recipient beginning to provide the speech response; and determining a length of the speech response provided by the recipient. In an example, detecting the response by the recipient includes determining a behavior of the recipient while the question is being asked. In an example, determining the behavior of the recipient includes measuring an amount or duration of stillness of the recipient while the question is being asked. In an example, measuring the amount or duration of stillness of the recipient includes: measuring muscle movement of the recipient using electromyography; measuring muscle movement of the recipient using a camera; measuring muscle movement of the recipient using an accelerometer; or measuring muscle movement of the recipient using a gyroscope. In an example, detecting the speech response includes: detecting a vocalization by the recipient using an implanted microphone; detecting a vocalization by the recipient using an external microphone; detecting a change in heart rate characteristic of an individual preparing to speak; detecting an intake of breath characteristic of an individual preparing to speak; detecting a cortical cascade of the recipient in response to the question. In an example, the auditory event is: a sing-song vocal activity, a spoken vocal activity, a sung vocal activity, an onomatopoeia vocal activity, a whispered vocal activity, or a musical activity. In an example, the response is a vocal reaction, a movement reaction, or a physiological reaction. In an example, the operations further include: classifying the auditory event as a relevant sensory event or an irrelevant sensory event. In an example, detecting the response by the recipient is performed responsive to the auditory event being classified as a relevant sensory event. In an example, the plurality of sensors include at least one sensor selected from the group consisting of: a microphone, a body noise sensor, a movement sensor, an implanted electrode sensor. In an example, the plurality of sensors include the movement sensor. In an example, the movement sensor is an accelerometer or gyroscope. In an example, taking the treatment action includes: modifying one or more settings of the auditory prosthesis; reporting a performance quality of the auditory prosthesis with respect to the auditory event; recommending corrective actions; or providing a metric estimating the recipient's ability to engage with the auditory event. In an example, the auditory prosthesis further includes memory storing instructions that, when executed by the one or more processors, cause the processor to perform the operations, thereby configuring the one or more processors to perform the operations. In an example, the stimulator comprises: a stimulator unit disposed within the housing; a stimulator assembly disposed at least partially outside of the housing; and an array of electrode contacts disposed on the stimulator assembly.

In an example, there is a non-transitory computer-readable medium comprising instructions that, when executed by one or more processors, cause the one or more processors to: receive event sensor data from a plurality of sensors proximate a recipient of a sensory prosthesis; detect an occurrence of a sensory event proximate the sensory prosthesis using the event sensor data; classify the sensory event as a relevant sensory event or an irrelevant sensory event; responsive to the sensory event being a relevant sensory event, detect a response by the recipient to the occurrence of the sensory event using response sensor data; characterize the response by the recipient using the response sensor data; and take a treatment action relating to the recipient based on the characterization.

In an example, the relevant sensory event is an event expected to elicit a characteristic reaction in the recipient. In an example, to characterize the response by the recipient includes to determine whether the sensor data is indicative of the recipient performing the characteristic reaction. In an example, to classify the sensory event as a relevant sensory event or an irrelevant sensory event includes to: analyze a location specified by the sensor data. In an example, to classify the sensory event as a relevant sensory event or an irrelevant sensory event includes to: compare a threshold with the sensor data; classify the sensory event as a relevant sensory event responsive to the sensor data satisfying the threshold; and classify the sensory event as an irrelevant sensory event responsive to the sensor data failing to satisfying the threshold. In an example, the instructions further cause the processor to: responsive to the sensory event being an irrelevant sensory event, refrain from detecting the response by the recipient to the occurrence of the sensory event. In an example, to take the treatment action includes to: modify a treatment operation of the sensory prosthesis by changing one or more settings of the sensory prosthesis. In an example, to characterize the response includes to: flag the response as being appropriate for the sensory event. In an example, the sensory prosthesis is an auditory prosthesis comprising the non-transitory computer-readable medium.

In an example, there is a system comprising: a non-transitory computer-readable medium comprising instructions that, when executed by one or more processors, cause the one or more processors to: selectively operate in a monitored mode or an unmonitored mode. While operating in the monitored mode: the instructions cause the one or more processors to receive sensor data from a plurality of sensors; detect an occurrence of a sensory event proximate a sensory prosthesis; characterize the sensory event; detect a response by the recipient to the occurrence of the sensory event using the sensor data; and store sensory event data regarding the sensory event and response data regarding the response by the recipient; and transition to the unmonitored mode. In an example, responsive to transitioning from the monitored mode to the unmonitored mode, transmit an analysis based on the sensory event data to a caregiver device.

In an example, to selectively operate in the monitored mode or the unmonitored mode includes to: operate in the unmonitored mode responsive to a proximity between the sensory prosthesis and the caregiver device. In an example, to selectively operate in the monitored mode or the unmonitored mode includes to: operate in the unmonitored mode based on a time of day. In an example, the instructions, when executed by the one or more processors, cause the one or more processors to, while in the unmonitored mode, refrain from detecting occurrences of sensory events proximate the sensory prosthesis. In an example, the analysis includes a metric describing an appropriateness of responses to the sensory event. In an example, to transmit the analysis to the caregiver device includes to: directly, automatically, and wirelessly transmitting the analysis from the sensory prosthesis to the caregiver device. In an example, the system further includes a first sensory prosthesis including first sensory prosthesis sensors; and the non-transitory computer-readable medium. In an example, the system further includes a secondary device comprising secondary device sensors. In an example, the instructions, when executed by one or more processors, further cause the one or more processors to: pool sensor output data from the first sensory prosthesis sensors and the secondary device sensors to form pooled data. In an example, detecting the occurrence of the sensory event proximate the recipient of the sensory prosthesis includes using the pooled data.

BRIEF DESCRIPTION OF THE DRAWINGS

The same number represents the same element or same type of element in all drawings.

DETAILED DESCRIPTION

Figure 1:
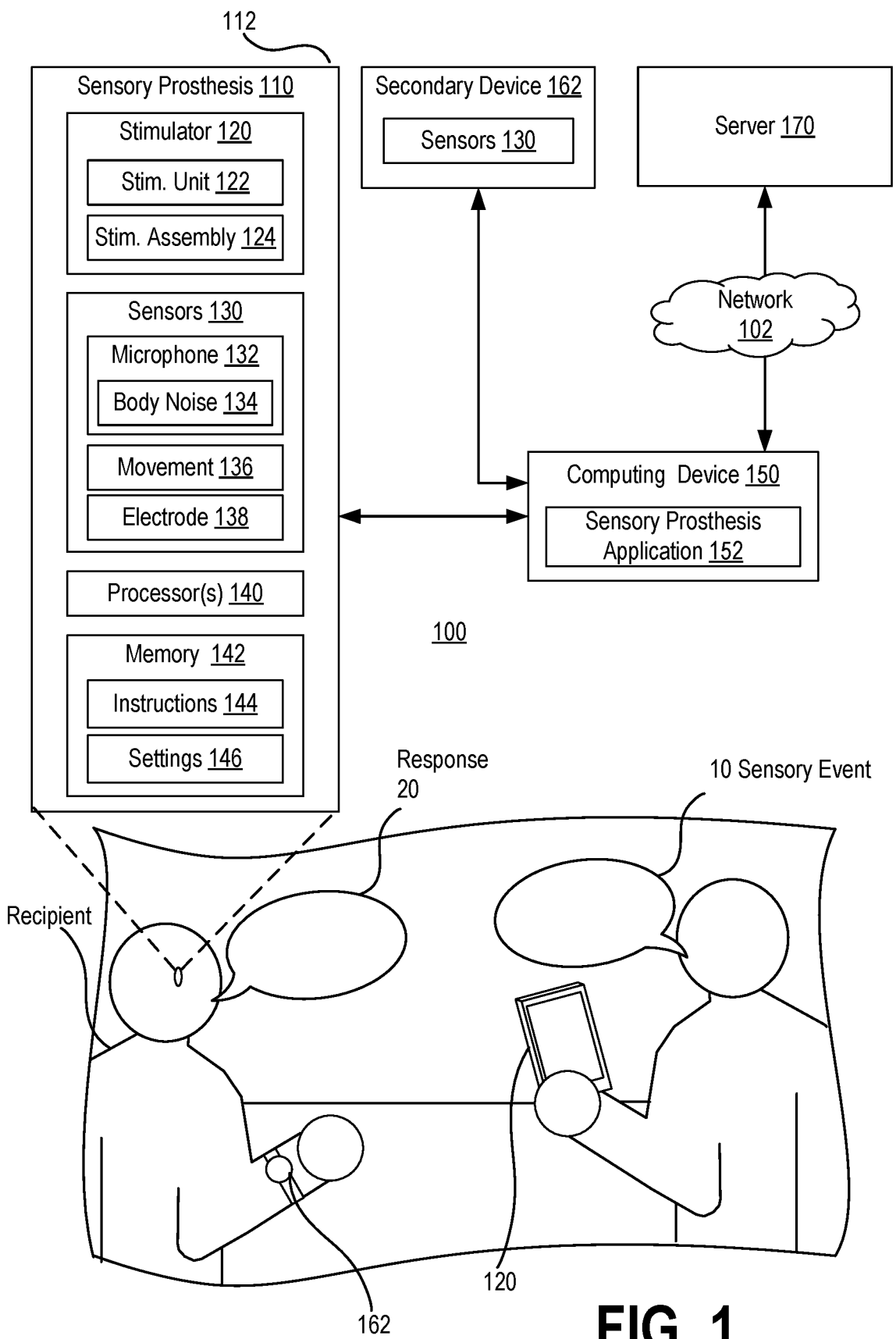
FIG. 1 illustrates a system with which one or more techniques described herein can be implemented.

To provide effective treatment interventions for individuals affected by loss of sensory abilities (e.g., hearing or vision loss), proper monitoring of the progression (or decline) of the individual's sensory capabilities is useful. Traditionally, the individual (or a caregiver thereof) is provided with a subjective verbal or written questionnaire regarding the individual's sensory abilities relative to those of a person having typical sensory capabilities. For example, where the relevant sense is hearing, a functional listening index can be used to determine relevant capabilities. A functional listening index is a metric that characterizes an individual's hearing performance with respect to common, everyday circumstances.

However, the traditionally subjective and intermittent nature of the analysis of an individual's sensory capabilities can limit the effectiveness of monitoring regimes and can produce low-quality data. Because treatment interventions are performed based on this data, improvements to data collection regarding sensory functioning of an individual results in improvements to treatment of the sensory condition of the individual.

Examples disclosed herein are relevant to improving the monitoring and treatment of sensory conditions affecting an individual, including an individual that is already the recipient of one or more sensory prostheses (e.g., auditory or visual prostheses). An example technology disclosed herein includes the use of sensors and intelligence integrated within a sensory prosthesis of a recipient to automatically obtain objective data regarding the performance of one or more of the recipient's senses during day-to-day activities. Further example technologies include technology for reducing the gathering of irrelevant sensory input (e.g., thereby improving the capability of the sensory prosthesis or another device to provide high-quality output on which treatment can be based) and automatically transmitting relevant data to a caregiver device.

In an example, a sensory event occurs proximate the recipient of a sensory prosthesis. Sensors of the sensory prosthesis obtain event data usable to detect the occurrence of the sensory event. Next, response data from the sensors is obtained and processed to characterize the recipient's response to the sensory event. The resulting characterization is used to take a treatment action regarding the recipient. For example, settings of the sensory prosthesis can be automatically modified to affect ongoing treatment of the recipient.

As particular examples, the techniques described herein can be applied to any of a variety of sensory events. With particular reference to auditory events, the event can be a conversation in a noisy restaurant and the characterization can indicate that the recipient of an auditory prosthesis had a difficult time hearing the other party. The settings of the auditory prosthesis can be modified to attempt to improve the performance of the auditory prosthesis in noisy environments. As another example, the auditory event can be positive or uplifting speech directed to the recipient. Such speech can have a distinctive signature (e.g., characteristic frequencies or tones) that can be detected. In response to such speech, the auditory prosthesis can determine whether the recipient is appropriately affected by the speech (e.g., a signal processing module can assess whether the recipient responds in a happy manner). Similar assessment can be conducted with respect to angry or upsetting speech directed at the recipient. The settings of the auditory prosthesis can be modified to improve reproduction for the particular characteristic frequencies or tones of the particular speech.

As can be seen in the example auditory events above, how well a recipient responds to vocalizations is a useful indicator of whether current treatment approaches are effective and whether they should be changed. Thus sensors of an auditory prosthesis can be used to detect and characterize an auditory event that includes speech into a category that is expected to elicit a characteristic reaction (e.g., answering a question, joining in with laughter, crying in response to shouting). The categorization can then be used to assess whether the recipient provided an appropriate response to the auditory event. More generally, how well a recipient responds to sensory events is a useful indicator of whether treatment approaches are working and should be changed.

Regarding the categorization, it can be determined whether there is a corresponding difference in responses provided by the recipient to auditory events belonging to particular categories or subcategories of auditory events (e.g., different types of questions, as determined by different tonal, frequency, or pitch characteristics). Likewise, in some examples, the auditory prosthesis assesses whether, in response to auditory events delivered with other sensory stimuli (e.g., speech in person, speech streamed with video, or speech streamed without video), there is a corresponding difference in responses provided by the recipient. Such categorization can be useful in identifying specific capabilities and deficiencies in the capability of an auditory prosthesis to cause hearing percepts in a recipient.

An auditory prosthesis can detect speech using a microphone (e.g., an implanted microphone or an external microphone of a sound processor). The detected speech can be analyzed to determine whether the detected speech is a type of speech that warrants a response by the recipient. For example, an integrated sound classifier or other intelligence can analyze the auditory event to determine whether the auditory event can be characterized as a question that warrants a response by the recipient. For instance, questions can typically be characterized in English by a rising intonation, which can be detected by an integrated sound classifier or intelligence of the auditory prosthesis. Questions can also have other signatures that can be detected in addition to or instead of intonation. In examples, the auditory event can be categorized using an accessory device (e.g., a mobile device, such as a phone or tablet, or a server). The categorization or a treatment action based thereon can be provided to the auditory prosthesis. In addition or instead, the characterization or the treatment action can be presented to the recipient or a caregiver.

After or during the sensory event, verbal or physiological signals from the recipient can be detected, classified, and logged. Physiological responses can include changes in heart and respiration activity (e.g., changes in rate, variation in rate, intervals between events, or the occurrence of arrhythmias) or neural activity (e.g., as measured by external or implanted sensors, such as a montage of electrodes, microphones, or accelerometers). The sensors used to detect such verbal or physiological responses can be a component of the sensory prosthesis (e.g., an implanted portion thereof or an external portion thereof, such as a sound processor) or a connected device (e.g., a phone or wearable). Movement and vocal responses can also be detected, classified, and logged.

Regarding vocal and other audible responses, a signal processing module (e.g., a hardware module or a software module) can process an audio signal captured via one or more sensors (e.g., an external or implanted microphone) and can be used to assess whether the recipient appropriately responded to the sensory event (e.g., responding appropriately to a question). For example, the audio signal can capture a vocalization by the recipient in response to the sensory event, such as a speech response. The module can measure the length of the speech response (or other vocalization) provided by the recipient and assess whether the length corresponds with the length of speech given by a typical response (e.g., a response to a question). Additionally, the module can determine how long the recipient took to vocally respond to the sensory event directed at the recipient. This data may also be relevant in computing a recipient's sensory abilities (e.g., a recipient's functional listening abilities). The module may also be used to evaluate the character of the response (e.g., intonation, frequency, pitch, etc.) to determine whether the response has the characteristics of an expected response.

Regarding movement responses, a signal processing module can process motion data obtained from one or more motion sensors (e.g., an accelerometer located in the sensory prosthesis itself or a companion device, such as a smart phone or smartwatch). The motion data can be used to, for example, assess whether the recipient appropriately responded to the question. For instance, the module can measure an amount and duration of the recipient's stillness while the recipient listens to a question, and an amount and duration of motion by the recipient while responding to the question.

Further, a recipient's ability to appropriately engage in mirroring behavior can be determined using the sensors. For example, mirroring can include the recipient mimicking playful language or motions directed at the recipient by a caregiver or for an answer by the recipient to contain similar words to the respective question. A signal processing module can be used to detect whether the recipient is appropriately engaging in mirroring using audio captured via a sensor, such as an external or implanted microphone. In particular, the system can detect (e.g., over an extended duration) if any tones, frequencies, other characteristics, or combinations thereof are absent in a recipient's mimicry.

In addition to or instead of the use of the sensors described herein, the signal processing module can process an electrophysiological signal obtained via one or more sensors (e.g., a montage or implanted or external electrodes) and can be used to assess whether the recipient appropriately responds to the auditory event. For example, the module may measure the duration of stillness while the recipient listens to a question and the duration of the response, via electromyography of the facial muscles. The module can measure the cortical cascade during central integration and processing of a heard question and during preparation of the spoken response.

In addition to or instead of the use of the sensors described herein, a signal processing module can process an audiophysiological signal captured via a sensor, such as an implanted microphone, and can be used to assess whether the recipient appropriately responds to the question. For example, the module can measure a change in heart rate or intake of breath while the recipient is preparing to respond to a sensory event.

In some examples, multiple sensory prostheses can cooperate to monitor a recipient's sensory ability. For example, bilateral auditory prostheses can be used in tandem to produce data to determine the recipient's ability to hear. When combined, the bilateral prostheses can pool their sensor data to feed a single signal processing module. In some examples, the bilateral prostheses can independently assess the sensory event and response before later combining the assessment into a single recipient record. In some examples, the prostheses may divide tasks (e.g., one prosthesis analyses sensory events and another prosthesis monitors the recipient's responses). Further, in response to changes in hardware configuration (e.g., bilateral, unilateral left, or unilateral right prosthesis configurations), it can be determined whether there is a corresponding difference in responses provided by the recipient. In particular, it can be determined whether the recipient's sensory functioning is better with a unilateral prosthesis or bilateral prostheses.

Advantageously, approaches described herein can beneficially preserve the recipient's privacy. The above approaches can be implemented without analyzing the actual content of speech (e.g., by measuring intonation of speech without performing speech-to-text analysis on the speech and analyzing the resulting text) when the sensory event or the response includes speech. For example, in certain implementations, the processing is performed on data regarding the quality of speech (e.g., intonation) and the processing can be devoid of the semantics of the speech. Of course, in other examples, analyzing the semantic content of speech can be beneficial in determining whether the recipient is responding appropriately. In some examples, the analysis of semantic content can be tied to a user-modifiable option such that the user can choose whether semantic content is analyzed.

The above techniques can be used to modify the treatment of sensory conditions affecting the recipient. For example, the techniques can be used to automatically or manually (e.g., with the help of a clinician) adjust mapping of an auditory prosthesis, or to provide feedback on past adjustments.

Example System

FIG. 1 illustrates a system 100 with which one or more techniques described herein can be implemented. As illustrated, the system 100 includes a sensory prosthesis 110 of a recipient (e.g., implanted in or worn by the recipient), a computing device 150, and a secondary device 162. The computing device 150 is connected to a server 170 over a network 102. The network 102 is a computer network, such as the Internet, that facilitates the electronic communication of data among computing devices connected to the network 102.

FIG. 1 further illustrates a sensory event 10 (e.g., an auditory or visual event) occurring proximate the recipient. And the recipient provides a response 20.

The sensory event 10 is an occurrence detectable by one or more human senses. In many examples, the sensory event 10 is an event expected (e.g., by a clinician) to be perceived by one or more normally-functioning and unaided human senses (e.g., a typical person is able to perceive a sound without an amplification device). While a sensory event 10 can often be perceptible by different human senses (e.g., someone speaking can often both be seen and heard speaking), the sensory event 10 can be limited to a specific sense that is being augmented by a sensory prosthesis of the recipient. The sensory event 10 can be an event expected to elicit a characteristic reaction in the recipient. In some examples, certain events for which a characteristic reaction from the recipient is not expected is excluded from consideration as a sensory event 10. For instance, white noise (e.g., fan noise or rain noise) can be sound heard by the recipient but for which a particular response is not expected.

The sensory event 10 can be an auditory event. The auditory event can be an occurrence that would typically cause a hearing percept in a human individual. For instance, the auditory event can have a volume greater than a threshold of typical human hearing and a frequency within a range of typical human hearing. In another example, the sensory event 10 can be a visual event. The visual event can be an occurrence that would typically cause a visual percept in a human individual. For example, the visual event can be within a spectrum and of an intensity visible to a typical human. In yet further examples, the sensory event can be a tactile sensory event, an olfactory sensory event, or a taste sensory event. The sensory event need not be limited to the five traditional senses, and can include, for example, equilibrioception, thermoception, proprioception, and nociception, among others.

Where the sensory event 10 is an auditory event, the auditory event can include one or more of the following auditory activities: a sing-song vocal activity, a spoken vocal activity, a sung vocal activity, an onomatopoeia vocal activity, a whispered vocal activity, and a musical activity. In an example, the sensory event 10 is an auditory event determined to likely cause a startle reaction (e.g., by having a particular loudness above a background level) in the recipient. The startle reaction of the recipient is an example of a response 20.

The response 20 is behavior by the recipient temporally proximate the occurrence of the sensory event 10. For instance, the temporal proximity can an amount of time in which a response by the recipient is expected to have occurred (if any response does occur). The amount of time can vary based on the type of sensory event (e.g., one may be expected to react more quickly to a startling event than a question). While, in many examples, the response 20 is a reaction by the recipient to the sensory event 10, the response 20 can include actions by the recipient that were not elicited by the sensory event 10. In other words, the recipient may fail to react to the sensory event 10, and even the failure to react can be considered a response 20 to the sensory event 10. Detecting such a non-reaction response 20 can be useful in modifying treatment actions. A non-reaction when a response is appropriate can indicate a gap between desired treatment outcomes and actual treatment outcomes.

The responses 20 can take any of a variety of forms. For example, the response 20 can include one or more of the following reactions: a vocal reaction (e.g., the recipient makes or fails to make a vocalization in response to the sensory event 10), a movement reaction (e.g., the extent to which the recipient moves or does not move in response to the sensory event 10), or a physiological reaction (e.g., the often involuntary physiological reactions that the recipient may make in response to the sensory event, such as increased blood flow, heart rate, or respiration rate).

Movement reactions can include large movement reactions, such as jumping, startling, or dancing. The movement reactions can be directional, such as the recipient looking or pointing in a particular direction. The movement reactions can also include subtle reactions, such as making a face (e.g., smiling). The movement reactions can further be a lack of movement or a change in movement (e.g., a relative decrease or increase in the amount of movement by the recipient) that may indicate that the recipient is listening to a person speaking or otherwise paying attention to a sensory event. The movement reactions can be detected based on movement data (e.g., obtained from accelerometers and gyroscopes) and electrode data (e.g., obtained from electrodes monitoring muscle movement or brain waves), among other sources. Predetermined thresholds can be used such that when particular data satisfies one or more thresholds, it can be determined that a movement reaction (or a specific kind of movement reaction) occurred. In addition or instead, machine learning can be used. For instance a machine learning framework can be trained to determine the occurrence of movement reactions (or specific kinds of movement reactions) based on input data.

Vocal reactions can include the recipient vocalizing a response. The vocalization can include, for example, speech, singing, laughter, or mimicry (e.g., of a sound, person, animal, or object), among others. The vocalization can include babbling or making sounds (e.g., making the Ling Six sounds or forming syllables without necessarily forming words). The vocalization can include the repetition of sounds, words or sentences. The vocalization can include answering questions or carrying on a conversation. The vocal reactions can be detected primarily based on audio data obtained from implantable or external microphones. The detection can include analyzing characteristics of the sounds (e.g., pitch, frequency, intensity, etc.) to determine whether and how the recipient is responding. The audio can be processed to facilitate the detection of the sounds. For example, speech-to-text processing can be performed on the speech and the resulting text can be analyzed to determine whether the recipient is properly responding to the sensory event 10 (e.g., by using natural language processing). Mimicry can be detected by comparing patterns in the characteristics of the response 20 with characteristics of the sensory event 10.

The responses 20 can include recognition reactions. Recognition reactions can be reactions demonstrating that the recipient understands or recognizes the sensory event 10. The recognition reaction can be an indication that the recipient understands or can tell the difference between different sensory events. For example, the recognition reaction can be telling the difference between talking or singing, understanding words or phrases, recognizing people by voice, can recognize emotion in a person's voice. The recognition reactions can be detected or inferred in a variety of ways. In an example, the recognition reactions are detected by analyzing brain waves (e.g., measuring a cortical cascade) of the recipient for patterns indicating recognition. In other examples, the recognition reaction can be inferred based on a movement (e.g., facial movement or larger muscle movement) or vocal response.

In some examples, the above-described reactions can form a complex reaction, such as one that includes both a vocal and movement response. In examples, a complex reaction can include the recipient following instructions and performing one or more actions in response. In some examples, the responses 20 (particularly complex reactions) can be detected based on a response from a person other than the recipient (e.g., a caregiver giving instructions). For instance, words of encouragement or disappointment can be used to infer whether a response 20 from the recipient was appropriate or inappropriate. Such content of speech can be determined through natural language processing (e.g., to analyzed the content) or via emotion detection.

Example System—Sensory Prosthesis

The sensory prosthesis 110 is an apparatus relating to one or more of the recipient's senses. For example, the sensory prosthesis 110 can be a prosthesis relating to one or more of the five traditional senses (vision, hearing, touch, taste, and smell) and/or one or more of the additional senses. For ease of understanding, many examples disclosed, the sensory prosthesis 110 is an auditory prosthesis medical device configured to treat a hearing-impairment of the recipient. Though many examples specific to auditory prostheses can be applicable to other kinds of sensory prostheses. Where the sensory prosthesis 110 is an auditory prosthesis, the sensory prosthesis 110 can take a variety of forms including a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, a tooth-anchored hearing device, a personal sound amplification product, other auditory prostheses, and combinations of the foregoing (e.g., binaural systems that include a prosthesis for a first ear of a recipient and a prosthesis of a same or different type for the second ear). In examples, the sensory prosthesis 110 can be or include features relating to vestibular implants and bionic eyes. Example implementations of the sensory prosthesis 110 are described in more detail in FIG. 5 (showing a cochlear implant), FIG. 6 (showing a percutaneous bone conduction device), FIG. 7 (showing a transcutaneous bone conduction device), and FIG. 8 (showing a retinal prosthesis). Technology disclosed herein can also be relevant to applications with devices and systems used in for example, sleep apnea management, tinnitus management, and seizure therapy. Technology disclosed herein can be used with sensory devices such as consumer auditory devices (e.g., a hearing aid or a personal sound amplification product).

As illustrated, the sensory prosthesis 110 includes a housing 112, a stimulator 120, one or more sensors 130, one or more processors 140, and memory 142. In many examples, the sensory prosthesis 110 can include more or fewer components than those shown in FIG. 1.

The housing 112 can include a wearable housing (e.g., wearable on a head of the recipient or a wrist of the recipient via a band, strap, magnetic connection, or another fastening technique). In some examples, the sensory prosthesis 110 can include multiple cooperating components disposed in separate housings. For example, the sensory prosthesis 110 can include an external component (e.g., having components to receive and process sensory data) configured to communicate with an implantable component (e.g., having components to deliver stimulation to cause a sensory precept in the recipient). Where the housing 112 is an implantable housing, the housing 112 can be made from a biocompatible material and hermetically seal an interior from intrusion of bodily fluid.

The stimulator 120 is one or more components of the sensory prosthesis 110 that provide stimulation to the recipient. For example, the stimulator 120 can receive stimulation control signals from another component of the sensory prosthesis and generate stimulation based thereon. The stimulator can apply the stimulation to the recipient to cause a sensory percept. The stimulation can take any of a variety of forms depending on the type of the sensory prosthesis. In many examples, the stimulation includes electrical stimulation or mechanical stimulation. The stimulator 120 can stimulate the recipient's nerve cells (e.g., in a manner that bypasses absent or defective cells that normally transduce sensory phenomenon into neural activity to cause a sensory percept in the recipient), in a manner that causes the recipient to perceive one or more components of sensory input data. As illustrated, the stimulator 120 can include a stimulator unit 122 and a stimulator assembly 124.

The stimulator unit 122 can be the portion of the stimulator 120 that generates the stimulation. For instance, where the stimulator 120 is an electrical stimulator, the stimulator unit 122 can generate electrical stimulation signals. Where the stimulator 120 is a mechanical stimulator, the stimulator unit 122 can be or include an actuator configured to generate vibrations.

The stimulator assembly 124 can be the portion of the stimulator 120 via which the stimulation is applied to the recipient. For example, where the stimulator 120 is an electrical stimulator of a cochlear implant, the stimulator assembly 124 can be an elongate lead having an array of electrode contacts disposed thereon for delivering the electrical stimulation to the recipient's cochlea. Where the stimulator 120 is a mechanical stimulator, the stimulator assembly 124 can be a plate, post, or another component to conduct vibrations from the stimulator unit 122 to a desired portion of the recipient's anatomy.

The sensors 130 are one or more components of the sensory prosthesis 110 that generate signals based on sensed occurrences, such as data regarding the environment around the sensory prosthesis 110, the sensory prosthesis 110 itself, or the recipient. In many examples, the sensors 130 are configured to obtain data for the generation of stimulation via the stimulator 120. In the illustrated example, the sensors 130 can include one or more: microphones 132, movement sensors 136, and electrode sensors 138.

The one or more microphones 132 can include one or more microphones implanted in the recipient or microphones external to the recipient. The microphones 132 can be transducers that convert acoustic energy into electric signals. One or more of the microphones 132 can be configured to receive sounds produced external to the recipient. One or more of the microphones can include or be configured as body noise sensors 134. The body noise sensors 134 are sensors 130 configured to sense body noises produced by the recipient. Body noises measurable by the body noise sensors 134 can include, for example, respiration sounds, blood flow sounds, heart beat sounds, or gut sounds, among other sounds.

The one or more movement sensors 136 can be transducers that convert motion into electrical signals. The movement sensors 136 can include, for example, accelerometers and gyroscopic sensors.

The one or more electrode sensors 138 can be one or more electrodes configured to detect electrical signals. In some examples, the electrode sensors 138 can be electrodes of the stimulator assembly 124 that are configured to not only deliver stimulation but also detect electrical signals. The electrode sensors 138 can include internal or external electrode sensors. In an example, the electrode sensors 138 are wearable electrodes, such as via a headband.

The sensors 130 can include one or more other sensors, such as one or more location sensors, telecoils, cameras, pupilometers, biosensors (e.g., heart rate or blood pressure sensors), otoacoustic emission sensors (e.g., configured to provide otoacoustic emission signals), EEG (electroencephalography) sensors (e.g., configured to provide EEG signals), one or more lights sensors configured to provide signals relating to light levels. The sensors 130 can include components disposed within a housing of the sensory prosthesis 110 as well as devices electrically coupled to the sensory prosthesis 110 (e.g., via wired or wireless connections).

In examples, the sensors 130 include one or more remote devices connected to the sensory prosthesis 110 via an FM (Frequency Modulation) connection, such as a remote microphone (e.g., a COCHLEAR TRUE WIRELESS MINI MICROPHONE2+), a television audio streaming device, or a phone clip device, among other devices having FM transmission capabilities. The sensors 130 can further include sensors that obtain data regarding usage of the sensory prosthesis 110, such as software sensors operating on the sensory prosthesis 110 that track data such as: when the sensory prosthesis 110 is worn by the recipient, when the sensory prosthesis 110 (e.g., an external portion thereof) is removed from the recipient, when one or more sensory prosthesis settings are modified, a current scene mode in which the sensory prosthesis 110 is operating (e.g., as determined by a scene classifier), and how long the sensory prosthesis 110 is operated using particular settings, among other data.

In examples, the sensors 130 can include a scene classifier. A scene classifier is software that obtains data regarding the environment around the sensory prosthesis (e.g., from one or more of the sensors 130) and determines a classification of the environment. The classifications can be used to determine settings appropriate for the environment. For example, where the sensory prosthesis 110 is an auditory prosthesis, the scene classifier can obtain data regarding the sonic environment around the auditory prosthesis and classify the sonic environment into one or more of the following possible classifications: speech, noise, and music, among other classifications. The sensory prosthesis 110 can then use the classification to automatically alter the sensory prosthesis settings to suit the environment. For example, responsive to the scene classifier determining that the sonic environment around the auditory prosthesis is windy, a wind-noise scene can be selected, which modifies settings of the auditory prosthesis to lessen wind noise. In another example, the scene classifier can determine that music is occurring nearby and automatically modify the auditory prosthesis settings to improve musical reproduction. An example scene classifier is described in US 2017/0359659, filed Jun. 9, 2016, and entitled "Advanced Scene Classification for Prosthesis", which is incorporated by reference herein in its entirety for any and all purposes.

The sensors 130 can produce sensor data. Sensor data is data produced by a sensor of the sensors 130. Sensor data can take any of a variety of different forms depending on the configuration of the sensor 130 that produced the sensor data. Further, the form and character of the sensor data can change as the sensor data is used and moved throughout the system 100. For example, sensor data can begin as a real-time analog signal that is converted into a real-time digital signal within a sensor 130, which is then transmitted in real-time as packets of data to an application for batch sending (e.g., non-real-time) to the server 170. Additionally, the sensor data can be processed as the sensor data are used and moved throughout the system 100. For instance, the sensor data can be converted into a standardized format and have relevant metadata attached (e.g., timestamps, sensor identifiers, etc.).

The one or more processors 140 are one or more hardware or software processing units (e.g., Central Processing Units) that can obtain and execute instructions. The one or more processors 140 can communicate with and control the performance of other components of the sensory prosthesis 110.

The memory 142 is one or more software- or hardware-based computer-readable storage media operable to store information accessible by the one or more processors 140. Additional details regarding memory are described in relation to FIG. 9. As illustrated, the memory 142 can store instructions 144 and sensory prosthesis settings 146.

The instructions 144 are processor-executable program instructions that, when executed by the one or more processors 140 cause the one or more processors 140 to perform actions or operations, such as the described in the processes herein. The instructions 144 can configure the one or more processors 140 to perform operations.

The sensory prosthesis settings 146 are one or more parameters having values that affect how the sensory prosthesis 110 operates. For example, the sensory prosthesis 110 receives sensory input from the environment (e.g., using a microphone of the sensory prosthesis 110 to obtain audio input), converts the sensory input into a stimulation signal, and uses the stimulation signal to produce stimulation (e.g., vibratory or electrical stimulation) to cause a sensory percept in the recipient.

The sensory prosthesis settings 146 can include a map having minimum and maximum stimulation levels for stimulation channels. The map is then used by the sensory prosthesis 110 to control an amount of stimulation to be provided. For instance, where the sensory prosthesis 110 is a cochlear implant, the map affects which electrodes of the cochlear implant to stimulate and in what amount based on a received sound input. In some examples, the sensory prosthesis settings 146 include two or more predefined groupings of settings selectable by the recipient. One of the two or more predefined groupings of settings may be a default setting.

The sensory prosthesis settings 146 can also include sensory processing settings that modify sensory input before the sensory input is converted into a stimulation signal. Such settings can include, in the case of an auditory prosthesis for example, particular audio equalizer settings can boost or cut the intensity of sound at various frequencies. In examples, the sensory prosthesis settings 146 can include a minimum threshold for which received sensory input causes stimulation, a maximum threshold for preventing stimulation above a level which would cause discomfort, gain parameters, intensity parameters (e.g., loudness), and compression parameters. The sensory prosthesis settings 146 can include settings that affect a dynamic range of stimulation produced by the sensory prosthesis 110. As described above, many of the sensory prosthesis settings 146 affect the physical operation of the sensory prosthesis 110, such as how the sensory prosthesis 110 provides stimulation to the recipient in response to sound input received from the environment. Thus modifying the sensory prosthesis settings 146 can modify treatment provided by the sensory prosthesis 110. Examples of settings, settings modification, and pre-processing for auditory prostheses are described in U.S. Pat. Nos. 9,473,852 and 9,338,567, which are both incorporated herein by reference for any and all purposes.

Example System—Computing Device

The computing device 150 is a computing device associated with the recipient of the sensory prosthesis 110. In many examples, the computing device 150 is a phone, tablet, smart watch, or heart rate monitor, but can take other forms. Although described primarily in the context of the recipient, the computing device 150 can be a computing device owned or primarily used by a parent or caregiver for the recipient. In the illustrated example, the computing device 150 includes a sensory prosthesis application 152. The computing device 150 can be in communication with the server 170, such as via the sensory prosthesis application 152 communicating over the network 102.

In examples, the computing device 150 includes a sensory prosthesis application 152 that operates on the computing device 150 and cooperates with the sensory prosthesis 110. The sensory prosthesis application 152 is a computer program stored as computer-executable instructions in memory of the computing device 150 that, when executed, performs one or more tasks relating to the sensory prosthesis 110. For instance, the sensory prosthesis application 152 can control the sensory prosthesis 110 (e.g., by modifying the sensory prosthesis settings 146 automatically or based on input received at the computing device 150 from the recipient), monitor usage of the sensory prosthesis 110, and obtain data from the sensory prosthesis 110. The computing device 150 can connect to the sensory prosthesis 110 using, for example, a wireless radiofrequency communication protocol (e.g., BLUETOOTH). The sensory prosthesis application 152 can transmit or receive data from the sensory prosthesis 110 over such a connection. The sensory prosthesis application 152 can be used to stream audio to the sensory prosthesis 110, such as from a microphone of the computing device 150 or an application running on the computing device 150 (e.g., a video or audio application). In other examples, another application running on the computing device 150 can stream sensory data to the sensory prosthesis 110. In examples, the sensory prosthesis application 152 functions as a source of data (e.g., a sensor 130) by obtaining data regarding the sensory prosthesis 110.

In some examples, one or more of the sensors 130 can be components of the computing device 150. For example, the computing device 150 can include hardware sensors or software sensors, such as software that obtains data from one or more data streams (e.g., audio or visual streamed from the computing device 150 to the sensory prosthesis 110).

Example System—Secondary Device

The secondary device 160 is a device separate from the sensory prosthesis 110 that can provide sensor data for use in performance of processes and operations described herein. In examples, the secondary device 160 is an additional sensory prosthesis 110 from which data can be obtained. In other examples, the secondary device can be a phone, tablet, smart watch, heart rate monitor, wearable EEG, smart ring, or other device having one or more sensors. The sensors can be as described above in relation to the sensors 130 of the sensory prosthesis 110. In some examples, the secondary device 160 can obtain data from secondary device sensors and transmit the data to one or more of the other devices or components of the system 100 for processing.

Example System—Server

The server 170 is a server computing device remote from the sensory prosthesis 110 and the computing device 150. The server 170 is communicatively coupled to the computing device 150 via the network 102. In many examples, the server 170 is indirectly communicatively coupled to the sensory prosthesis 110 through the computing device 150 (e.g., via the sensory prosthesis application 152). In some examples, the server 170 is directly communicatively coupled to the sensory prosthesis 110 (e.g., via a wireless telecommunications data connection of the sensory prosthesis 110). In certain examples, the sensory prosthesis 110 and the computing device 150 can be considered client devices of the server 170. In some examples, the functionality provided by the server 170 or the components thereof can be provided by or located on a device local to the recipient (e.g., the computing device 150 or the sensory prosthesis 110). The sensory prosthesis application 152 can be a client application configured to interact with the server 170. The server 170 can include a processing unit and memory, which are described in more detail in FIG. 9. The server 170 can further includes instructions executable to perform one or more of the operations described herein.

Example Processes

Figure 2A:
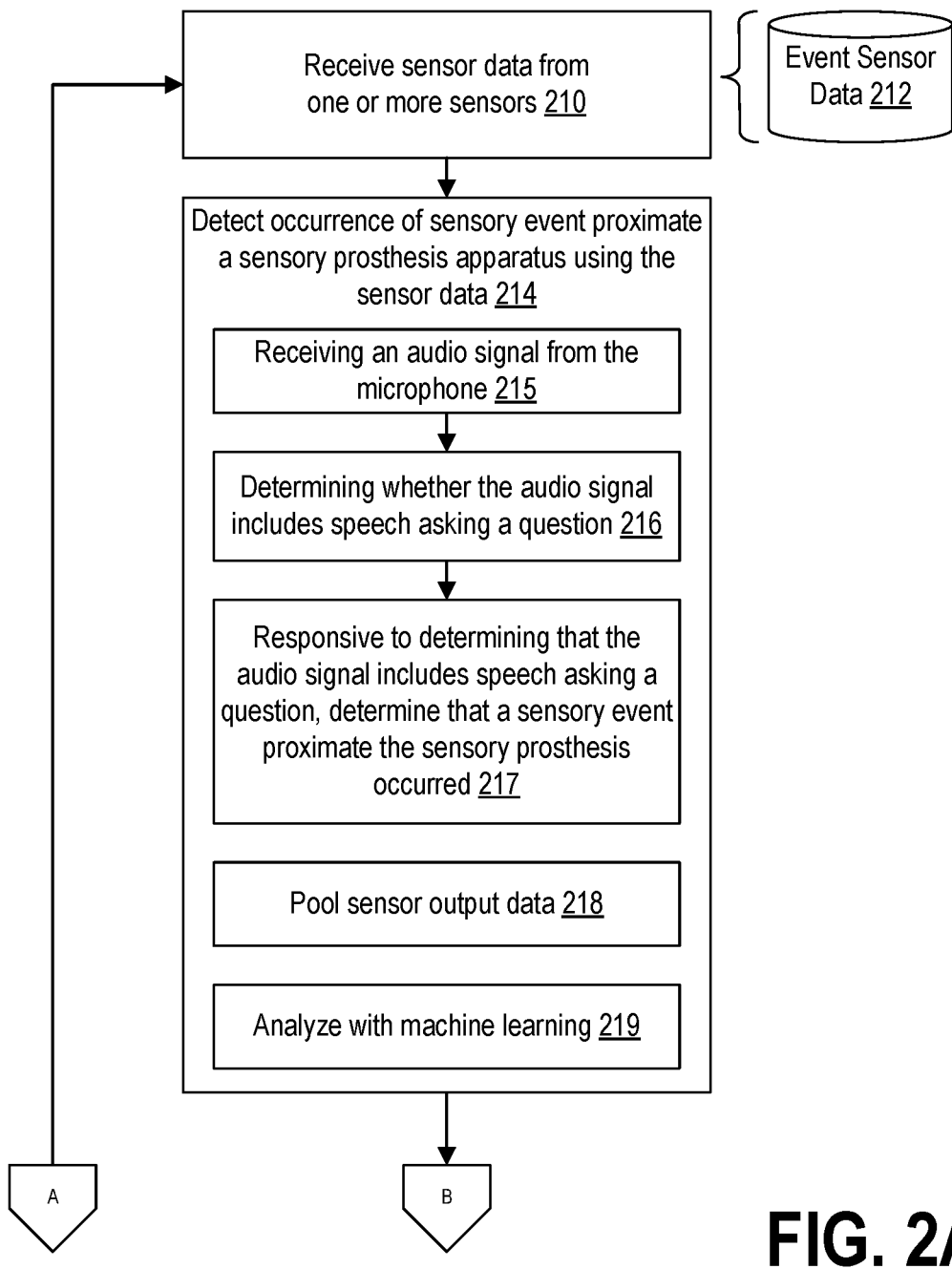
FIG. 2, which is made up of FIGS. 2A-2E, illustrates a first example process for monitoring an individual's sensory capabilities and taking a treatment action based thereon.
Figure 2B:
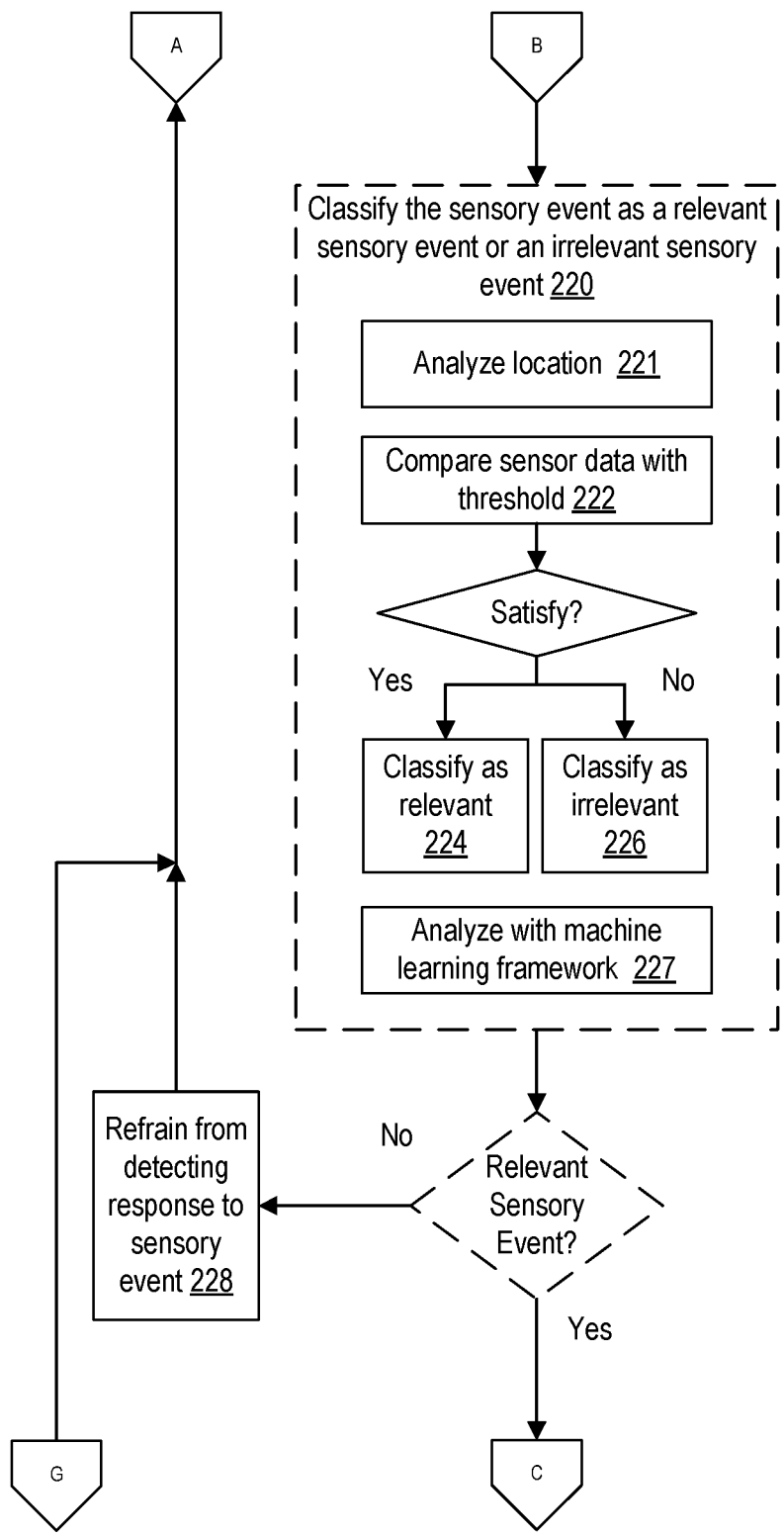
Figure 2C:
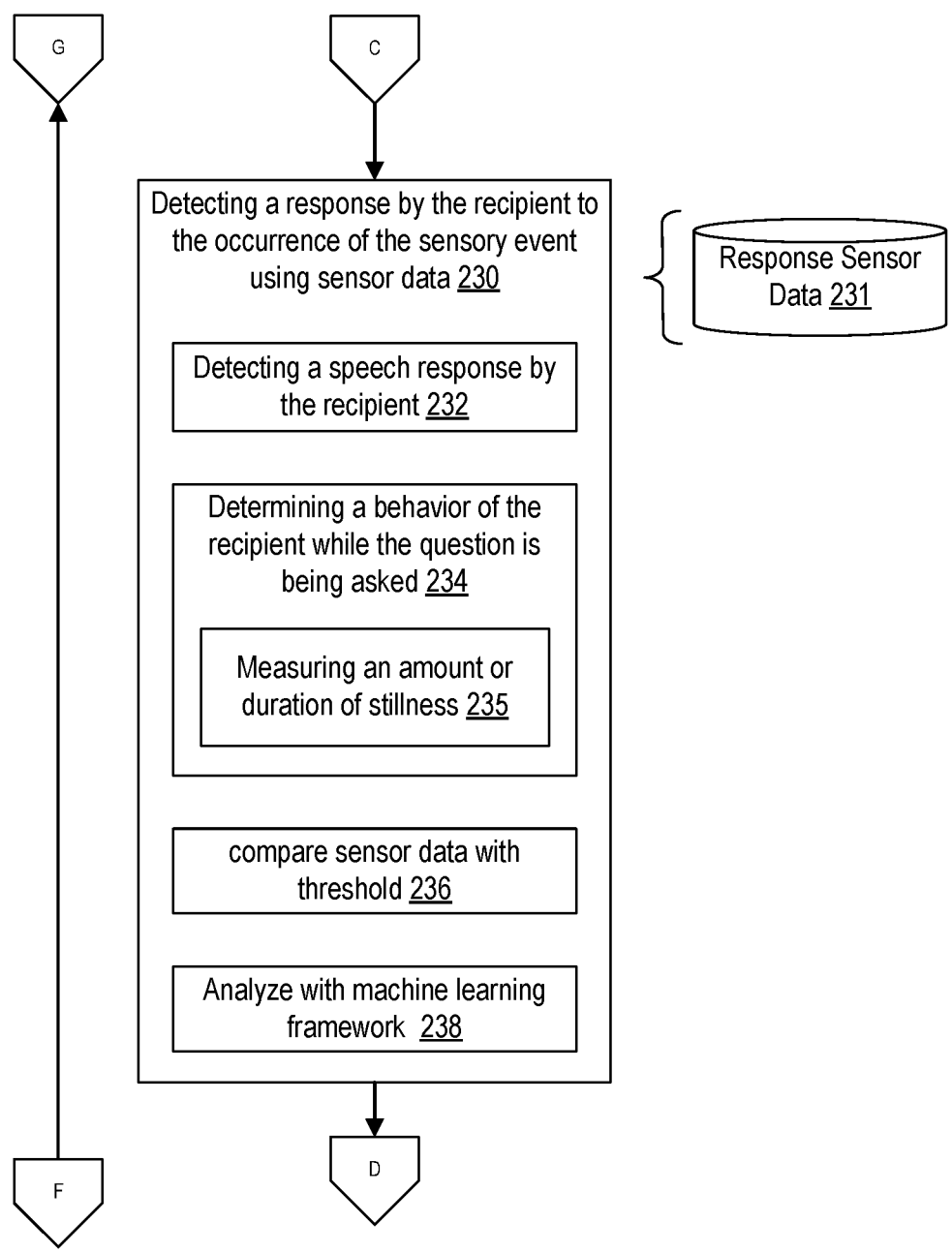
Figure 2D:
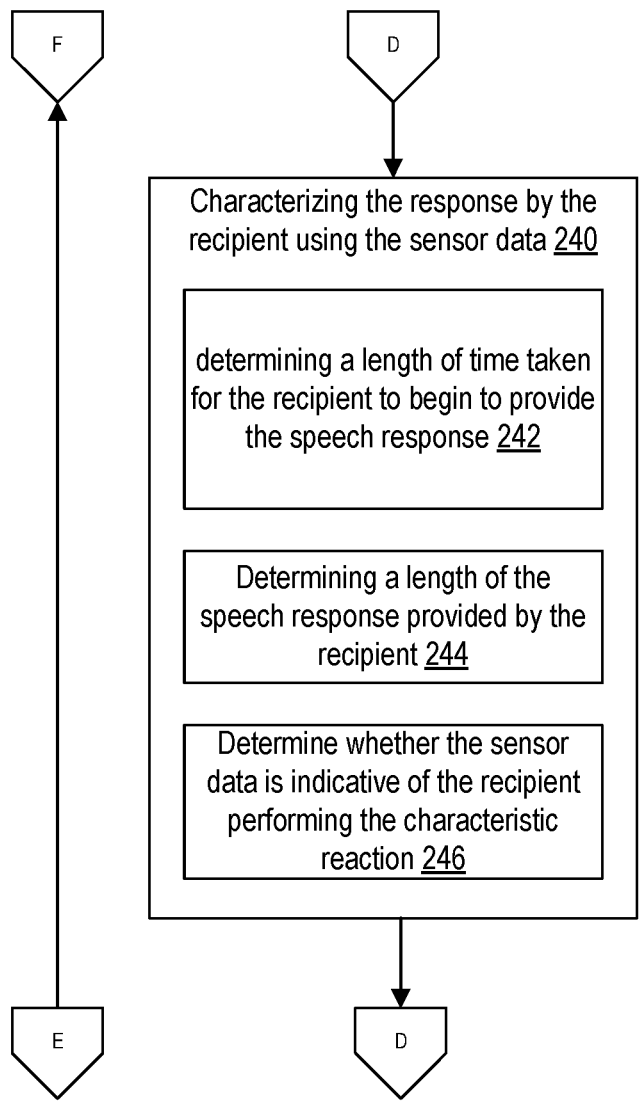
Figure 2E:
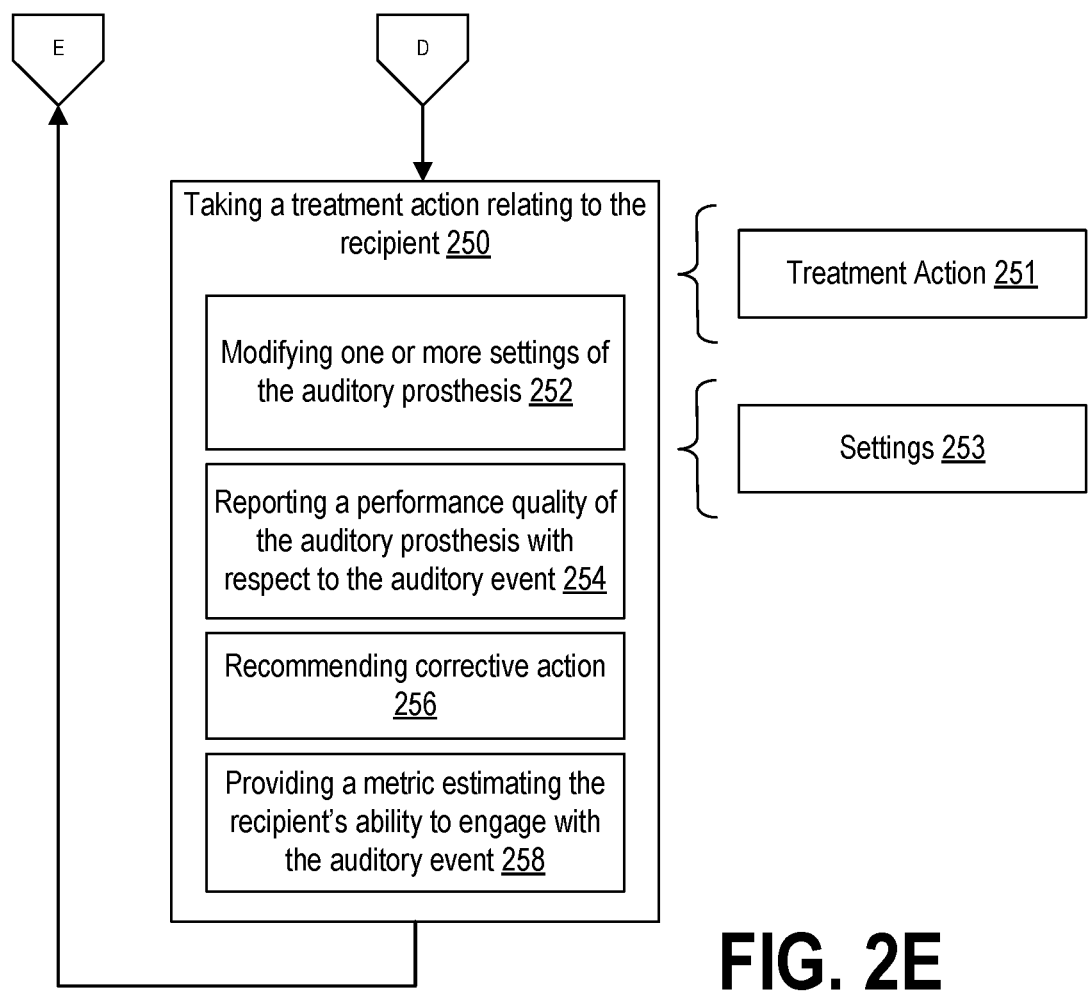
Figure 3:
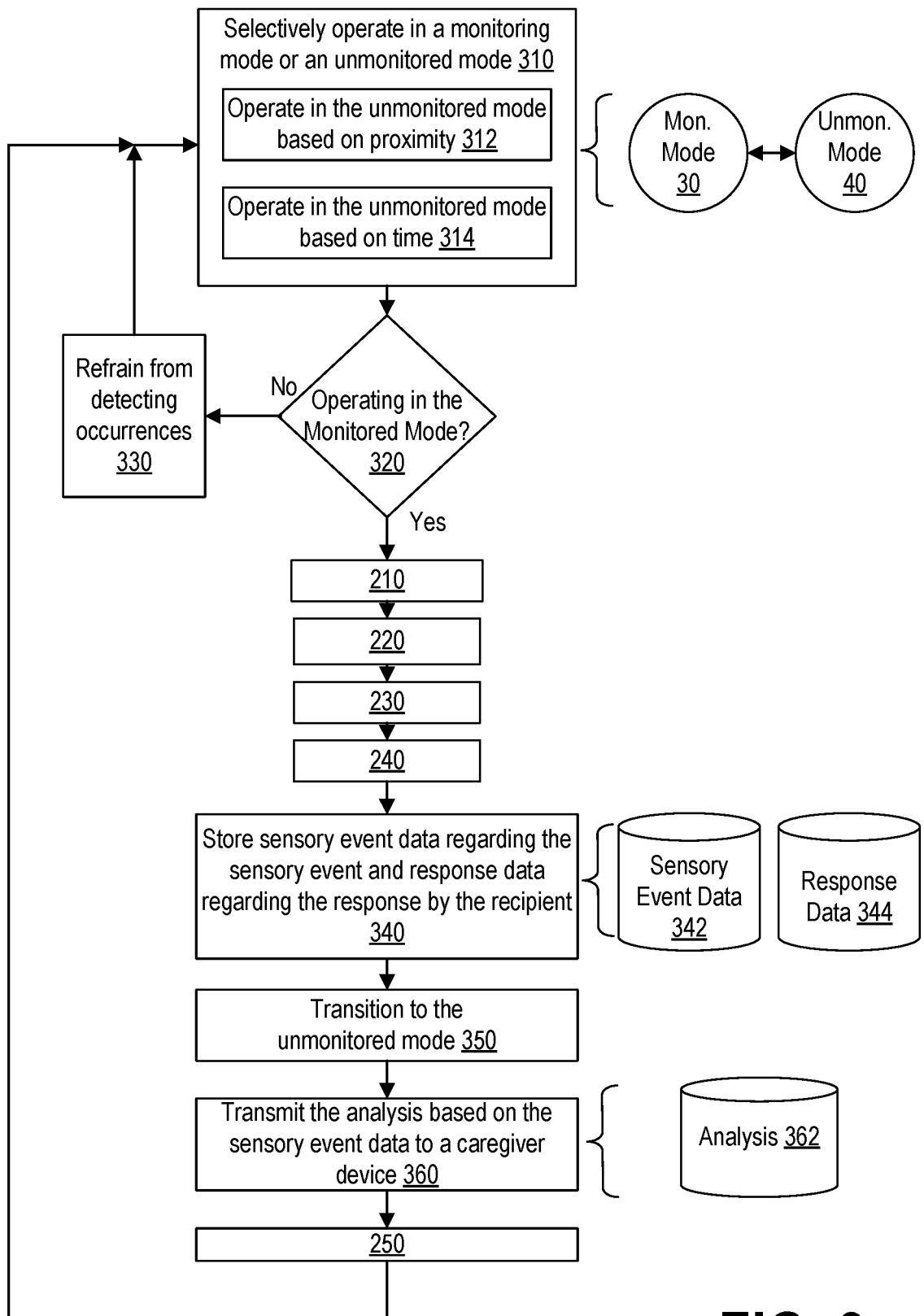
FIG. 3 illustrates a second example process for monitoring an individual's sensory capabilities and taking a treatment action based thereon.

FIG. 2 and FIG. 3 illustrate example processes for monitoring an individual's sensory capabilities and taking a treatment action based thereon. One or more aspects of the processes (e.g., one or more operations thereof) can be implemented as one or more instructions stored as part of the instructions 144. For ease of understanding, the processes are written with the sensory prosthesis 110 preforming the operations. However, the processes can modified to be performed at least in part by one or more other devices, such as the computing device 150, the secondary device 162, the server 170, other devices, or combinations thereof. One or more of the devices can have instructions that, when executed, cause performance of one or more of the operations.

Example Process—First Example Process

FIG. 2, which is made up of FIGS. 2A-2E, illustrates an example process 200. In examples, the process 200 begins with operation 210.

Operation 210 includes receiving event sensor data 212 from one or more of the sensors 130. The event sensor data 212 can be received in any of a variety of ways. The event sensor data 212 can be received directly from the sensors 130 themselves or via an intermediary device. For example, at least some of the event sensor data 212 can be transmitted via the secondary device 162 or the computing device 150 to the sensory prosthesis 110 for processing. In some examples, the event sensor data 212 is pushed to the sensory prosthesis 110. In other examples, the sensory prosthesis 110 sends a request to the sensors 130 or a device associated therewith to obtain the event sensor data 212.

In some examples, the event sensor data 212 is stored prior to processing by the sensory prosthesis 110. In some examples, the sensory prosthesis 110 periodically obtains readings from the sensors 130. The sensory prosthesis can collect the event sensor data 212 at a variety of frequencies and the amount of event sensor data 212 can likewise vary. For instance, in some examples, the obtaining and transmitting the event sensor data 212 occurs without substantial delay (e.g., in real-time). In other examples, the devices that include sensors 130 can obtain and store the event sensor data 212 in batches of data and transmit the event sensor data 212 less frequently to the sensory prosthesis 110.

In an example, the operation 210 includes receiving movement sensor signals from one or more movement sensors 136. In an example, receiving movement sensor signals can include receiving accelerometer signals from an accelerometer of the sensory prosthesis 110, receiving gyroscope signals from a gyroscope of the sensory prosthesis 110, receiving accelerometer signals from an accelerometer of the secondary device 162, or receiving gyroscope signals from a gyroscope of the secondary device 162. In an example, the operation 210 includes receiving body noise sensor signals from a body noise sensor 134 (e.g., an implanted microphone 132). In an example, the operation 210 includes receiving implanted or external electrode sensor signals from the implanted or external electrode sensor 138. In an example, the operation 210 includes receiving external microphone signals from an external microphone 132. Following operation 210, the flow can move to operation 214.

Operation 214 includes detecting the occurrence of a sensory event 10 proximate a sensory prosthesis 110 using the event sensor data 212. Detecting the occurrence of the sensory event 10 can include comparing the event sensor data 212 to or with one or more templates relating to determining the occurrence of a sensory event 10. For example, the templates may include one or more thresholds relating to the event sensor data 212 (e.g., audio data, movement data, or another kind of data) that indicate that a sensory event 10 occurred. In another example, the templates include one or more machine-learning frameworks configured to receive at least some of the event sensor data 212 as input and, as output, provide a prediction regarding whether or not a sensory event 10 occurred.

In an example, the occurrence of the sensory event 10 can be determined responsive to the sensory prosthesis 110 operating in a specific sensory processing mode based on a determination by a scene classifier of the sensory prosthesis 110. In an example, where the sensory event 10 is a speech event (e.g., another person speaking to the recipient) the occurrence of the sensory event 10 can be determined responsive to the scene classifier operating in or switching to operating in a speech-processing mode. In an example, the occurrence of the sensory event 10 is determined based on user input. For example, the recipient (or a caregiver or another person) can provide user input (e.g., at the sensory prosthesis 110 directly or at another device) indicating that a sensory event 10 is occurring or has recently occurred. In some examples, the user input can further specify a kind of sensory event (e.g., speech, music, etc.).

As another example, operation 210 can include determining the occurrence of a sensory event 10 proximate the recipient based on location data of the event sensor data 212. The location data can be useful in determining whether the recipient is in a location where a specific kind of sensory event 10 is likely to take place. For example, location data indicating that the recipient is at a movie theater can increase the likelihood that the recipient is experiencing sensory events that typically occur during movies. As another example, location data indicating that the recipient is at a school can increase the likelihood that the recipient is experiencing sensory events typical of that of a classroom (e.g., a lecture sensory event).

In an example, location data can include satellite-based location data (e.g., GPS-based location data) generated by the computing device 150. In another example, the location data is based on nearby wireless broadcasts, such as WI-FI SSIDs (Service Set Identifiers). Such wireless broadcasts can be useful for determining a current location as well as a current location type. For instance, while the sensory prosthesis 110 is operating in a school, the computing device 150 may detect a WI-FI SSID called "Classroom Wi-Fi", which can be used as an indication that a school sensory event is occurring or likely to occur. In another example, the location data can be determined based on the recipient manually or automatically checking-in at a location (e.g., using the computing device 150).

In some examples, detecting the occurrence of the sensory event 10 can include determining whether an audio signal includes speech that likely warrants a response. For instance, the speech can be the recipient's name being spoken, a command, a part of a conversation, or a question. Detecting whether speech warrants a response can include determining characteristics (e.g., frequencies, amplitude modulation, and spectral spread of the audio signal) of the speech and comparing the characteristics with thresholds. The analysis can further include the use of machine learning to analyze the speech. Examples relating to the speech that likely warrants a response being a question are described in more detail in operations 215-217.

In some examples, operation 210 or 214 includes operation 215. Operation 215 includes receiving an audio signal from a microphone 132 (e.g., in some examples, the sensors 130 can include the microphone 132) as part of the event sensor data 212. The microphone 132 can be an external or implantable microphone (e.g., of the sensory prosthesis 110) that produces an audio signal indicative of the sonic environment proximate the recipient.

Following operation 215, the flow can move to operation 216. Operation 216 includes determining whether the audio signal includes speech asking a question. The audio signal can be analyzed by, for example, the sensory prosthesis 110, the computing device 150, the server 170, another device, or combinations thereof. In an example, the audio signal can be analyzed to determine whether the qualities of the audio signal indicate the occurrence of a sensory event 10. For example, the frequencies, amplitude modulation, and spectral spread of the audio signal can be analyzed (e.g., using templates 180) to determine whether a threshold of likelihood is satisfied that indicates the likely occurrence of a sensory event 10. In particular, the analysis can be performed to determine whether the audio signal includes speech asking a question. In some examples, the analysis of whether the audio signal includes speech asking a question can include determining an increasing pitch in the audio signal.

Following operation 216, the flow can move to operation 217. Operation 217 includes determining that a sensory event 10 (e.g., an auditory event) proximate the sensory prosthesis 110 (e.g., an auditory prosthesis) occurred. The determining can include setting a flag or otherwise writing data indicating that the sensory event 10 occurred. In examples, operation 217 can be performed responsive to determining that the audio signal includes speech asking a question in operation 216.

In some examples, operation 210 or 214 includes operation 218. Operation 218 includes pooling sensor output data. For example, pooling sensor output data can include pooling sensor output data from sensors of multiple different sensory prostheses (e.g., pooling output data from first sensory prosthesis sensors and second sensory prosthesis sensors) to form pooled data. Then the detection of the occurrence of the sensory event proximate the recipient can include the use of the pooled data. In some examples, the event sensor data 212 is pooled or the event sensor data 212 is the pooled data.

In some examples, operation 214 includes operation 219. Operation 219 includes determining whether a sensory event 10 occurred by analyzing or processing the event sensor data 212 with a machine-learning framework. For example, some or all of the event sensor data 212 may be provided as input into a machine-learning framework configured to process input and provide, as output, an indication of whether the input data indicates that a sensory event 10 occurred. Additional details regarding the use of a machine-learning framework are described in relation to FIG. 4.

Following operation 214, the flow can move to operation 220 (see FIG. 2B). Operation 220 includes classifying the sensory event 10 as a relevant sensory event or an irrelevant sensory event. Advantageously, this classification can facilitate improvements to processing efficiency by allowing for irrelevant sensory events 10 to be disregarded or by allowing for relevant sensory events 10 to be focused. In some examples, a relevant sensory event 10 is a sensory event 10 likely to elicit a response 20 from the recipient. In some examples, a relevant sensory event 10 is a sensory event 10 of interest (e.g., to the recipient, caregiver, or a clinician). For example, a caregiver may be interested in sensory events 10 that occur while the caregiver is not present (e.g., as may occur at school or daycare). So the relevant sensory events 10 can be sensory events 10 that occur remote from the caregiver (e.g., as may be determined via geofencing or based on distance between a caregiver device and the sensory prosthesis 110). As another example, the recipient may be testing updated settings configured to improve performance of the sensory prosthesis 110 with respect to classroom sensory events, so the relevant sensory events 10 can be sensory events 10 that occur at a classroom. In some examples, the relevance can be customized (e.g., by the recipient, a caregiver, or a clinician). For example, relevant sensory events can be customized to be age-appropriate for a recipient. For instance, relevance for infants (e.g., sound events likely to cause a startle reflex in the infant) will likely be different from relevance for adolescents (e.g., adolescents would likely respond to speech differently from infants). The classification can be performed in any of a variety of ways, such as based on location (see, e.g., operation 221), thresholds (see, e.g., operation 222), machine-learning frameworks (see, e.g., operation 227), other ways, or combinations thereof.

In some examples, operation 220 includes operation 221. Operation 221 includes analyzing a location. For example, the location can be determined or inferred from the event sensor data 212 (e.g., using satellite-based location data or nearby wireless broadcasts as described above). The location of the sensory prosthesis 110 can be compared to a predetermined location. Responsive to the comparison being satisfied, the sensory event 10 can be classified as a relevant sensory event. Responsive to the comparison not being satisfied, the sensory event 10 can be classified as an irrelevant sensory event. The comparison can be satisfied in any of a variety of ways, such as the distance between the location of the sensory prosthesis 110 and the predetermined location being less than or equal to a threshold distance apart. In another example, the comparison can be satisfied based on a particular wireless broadcast (e.g., WI-FI SSID) being detectable or undetectable by the sensory prosthesis 110 or another device associated with the recipient.

In some examples, operation 220 includes operation 222. Operation 222 includes comparing one or more thresholds with some or all of the event sensor data 212. The thresholds can be predetermined thresholds of relevance. For example, the one or more thresholds can be an amount of a characteristic of the sensory event before a typical person is able to sense or is expected to respond to the sensory event 10. In another example, a threshold is an amount of a characteristic of the sensory event 10 before the recipient is able to sense or is expected to respond to the sensory event 10 (e.g., where the recipient has a higher or lower ability to sense the sensory event than a typical person). A threshold can be a level of intensity (e.g., decibels or lumens) before a response is expected. In such examples, a decibel level of the event sensor data 212 is compared with a decibel level that is a threshold of typical human hearing. The operation 222 can include comparisons with multiple different thresholds of the one or more thresholds before the operation 222 is completed.

Responsive to the event sensor data 212 satisfying the one or more thresholds, the flow can move to operation 224. Operation 224 includes classifying the sensory event 10 as a relevant sensory event 10 responsive to the event sensor data 212 satisfying the one or more thresholds. Responsive to the event sensor data 212 not satisfying the one or more thresholds, the flow can move to operation 226. Operation 226 includes classifying the sensory event 10 as an irrelevant sensory event responsive to the sensor data failing to satisfy the one or more thresholds. Classifying the sensory event 10 as being relevant or irrelevant can include setting a flag or otherwise storing data indicating the relevance of the event. In some examples, data regarding irrelevant events is discarded.

In some examples, operation 220 includes operation 227. Operation 227 includes determining a relevance of the sensory event 10 with a machine-learning framework. For example, some or all of the event sensor data 212 may be provided as input into a machine-learning framework configured to process input and provide, as output, an indication of whether the input data indicates that a sensory event 10 is relevant or irrelevant. Additional details regarding the use of a machine-learning framework are described in relation to FIG. 4.

Following operation 220 and responsive to the sensory event being an irrelevant sensory event, the flow can move to operation 228. Operation 228 includes refraining from detecting the response 20 by the recipient to the occurrence of the irrelevant sensory event 10. This refraining from detection can conserve battery and computing resources of the sensory prosthesis 110. Following operation 228, the flow can return to operation 210 (see FIG. 2A).

Following operation 220 and responsive to the sensory event being a relevant sensory event, the flow can move to operation 230.

Operation 230 includes detecting a response 20 by the recipient to the occurrence of the sensory event 10 using response sensor data 231. The response sensor data 231 is data obtained from one or more of the sensors 130 usable to detect whether a recipient had a response 20 to the sensory event 10. In some examples, the response sensor data 231 is or includes the same event sensor data 212 used to detect the occurrence of the sensory event 10. For example, the event sensor data 212 can include sufficient data (e.g., data covering a sufficiently long timespan) to cover both the occurrence of the sensory event 10 and the response 20. In some examples, additional data is collected from the sensors 130 to cover the time of the recipient's response 20. The additional data can be added to the event sensor data 212 to form the response sensor data 231. In some examples, portions of the event sensor data 212 can be discarded when at least some of the event sensor data 212 is used as the response sensor data 231. Further, response sensor data 231 useful for detecting the response 20 can be different from the event sensor data 212. For instance, motion sensors that track motion of the recipient are likely useful in determining the recipient's response 20 to the sensory event 10 but are unlikely to determine whether the sensory event 10 occurred (unless, for example, the sensory event 10 is a tactile sensory event 10). The response sensor data 231 can be obtained in a similar manner to the collection of the event sensor data 212 described above.

In some examples, operation 230 includes operation 232. Operation 232 includes detecting a speech response by the recipient. Detecting the speech response can include detecting a vocalization by the recipient. The vocalization can be detected in any of variety of ways. For example, the vocalization can be detected using an implanted or external microphone 132. Audio data from the microphone 132 can be analyzed (e.g., characteristics of the audio data can be compared to one or more thresholds for frequency, pitch, volume, or other characteristics) to determine whether the recipient vocalized a response. In addition to or instead of using audio data to identify the speech response, the operation 232 can include detecting a change in heart rate characteristic of the recipient preparing to speak or currently speaking. For example, an intake of breath characteristic of the recipient preparing to speak or currently speaking can be detected. As another example, a cortical cascade of the recipient preparing to or currently speaking can be detected. In addition, the cortical cascade can be indicative of the recipient responding to a question (e.g., the question detected in operation 216).

In some examples, operation 230 includes operation 234. Operation 230 can include operation 234 when the sensory event 10 includes a question being asked (e.g., the question detected in operation 216). Operation 234 includes determining a behavior of the recipient while the question is being asked. In some examples, operation 234 includes operation 235. Operation 235 can include measuring an amount or duration of stillness by the recipient. In some examples, measuring the amount of duration or stillness by the recipient can include measuring muscle movement of the recipient. For example, measuring the muscle movement can be performed using electromyography, a camera, an accelerometer, a gyroscope, or another sensor. Stillness of the recipient can be used to infer that the recipient is listening to the question (and therefore can hear the question and is responding appropriately).

In some examples, operation 230 includes operation 236. Operation 236 includes comparing the response sensor data 231 with one or more predetermined thresholds. Responsive to the response sensor data 231 satisfying the one or more thresholds, it can be determined that a response 20 occurred.

Responsive to the response sensor data 231 failing to satisfy the one or more thresholds, it can be determined that a response 20 did not occur.

In some examples, operation 230 includes operation 238. Operation 238 includes determining whether a response 20 occurred using a machine-learning framework. For example, some or all of the response sensor data 231 can be provided as input into a machine-learning framework configured to process input and provide, as output, an indication of whether the input data indicates that a response 20 occurred. Additional details regarding the use of a machine-learning framework are described in relation to FIG. 4.

Following operation 230, the flow can move to operation 240 (see FIG. 2D). Operation 240 includes characterizing the response 20 by the recipient using the event sensor data 212. In examples, characterizing the response 20 can include flagging the response 20 as being appropriate for the sensory event 10. As previously described, the response 20 can be a lack of an appropriate reaction. For instance, if the recipient's movement is relatively unchanged before, during, and after a question is asked proximate the recipient, the response can be determined to be inappropriate. The appropriate response 20 can be the recipient being still or exhibiting reduced movement during or after the question being asked. Characterizing the response 20 as being appropriate or inappropriate can include comparing the actual response with an expected appropriate response from a typical individual or the recipient.

In some examples, operation 240 includes operation 242. Operation 242 includes determining a length of time taken for the recipient to begin to provide a speech response in response to the sensory event 10. For instance, the length of time taken can be a time taken from sensory event 10 occurring (e.g., the question being asked) to the recipient beginning to provide the speech response. In examples, the recipient beginning to provide the speech response can be detected responsive to the detecting a change in heart rate, change in cortical activity, or intake of breath. Responsive to the length of time being less than a threshold amount of time, the response 20 can be characterized as being appropriate. Otherwise, the response 20 can be characterized as being inappropriate.

In some examples, operation 240 includes operation 244. Operation 244 includes determining a length of the speech response provided by the recipient. The length of the speech response provided by the recipient can be determined using, for example, data obtained from an internal or external microphone. Responsive to the length of the speech response being less than a threshold amount of time, the response 20 can be characterized as being appropriate. Otherwise, the response 20 can be characterized as being inappropriate.

In some examples, operation 240 includes operation 246. Operation 246 includes determining whether the response sensor data 231 is indicative of the recipient performing a characteristic reaction. This can include comparing the response sensor data 231 to predetermined thresholds associated with characteristic reactions. For instance, there can be an amount of movement below which indicates that a recipient is having an appropriate listening reaction to hearing a speech sensory event 10. There can be an amount of activity detectable in the response sensor data 231 indicating that the recipient is moving in response to a sensory event 10 (e.g., dancing or performing another action).

In some examples, characterizing the response 20 includes characterizing the response using a machine-learning framework. For example, some or all of the response sensor data 231 can be provided as input into a machine-learning framework configured to process input and provide, as output, a characterization of the response 20. Additional details regarding the use of a machine-learning framework are described in relation to FIG. 4.

Following operation 240, the flow can move to operation 250 (see FIG. 2E). Operation 250 includes taking a treatment action 251 relating to the recipient. The treatment action 251 can relate to improving the ability of the recipient to respond to sensory events 10, such as by improving the ability of the sensory prosthesis 110 to cause sensory percepts in the recipient. In an example, the treatment action 251 is an action relating to the treatment of a medical condition associated with one or more of the recipient's senses. Based on the characterization of the response 20, various treatment actions 251 can be performed, selected, determined, or recommended.

In an example, the treatment action 251 includes reporting a performance quality of the sensory prosthesis 110 with respect to the sensory event 10, such as to a clinician (e.g., to help guide treatment) or caregiver (e.g., to help assure the caregiver that the sensory prosthesis 110 is functioning as intended).

The treatment action 251 can also include using characterization of the response 20 as input to a rehabilitation program. The rehabilitation program can take any of a variety of forms and can generally relate to rehabilitating the recipient to more appropriately respond to sensory events 10. An example rehabilitation game is BRING BACK THE BEAT smartphone application by COCHLEAR LTD which relates to improving the ability of a recipient to respond to musical sensory events.

In some examples, operation 250 includes operation 252. Operation 252 includes modifying one or more settings 253 of the sensory prosthesis 110. In this operation 252, modifying the settings 253 can result in the modification of the treatment operation of the sensory prosthesis. Based on the characterization of the response 20 (e.g., the response 20 being appropriate or inappropriate), it can be determined that the sensory prosthesis settings 146 are sub-optimally causing sensory percepts in the recipient with respect to particular sensor events and that one or more changes to the sensory prosthesis settings 146 can improve the performance of the sensory prosthesis 110 with respect to the sensory event 10. Based on the determination, information regarding the one or more changes can be provided to the recipient, a caregiver, or a clinician (e.g., by way of a report). In some examples, the one or more changes are be automatically adopted by the sensory prosthesis 110 itself. The sensory prosthesis settings 146 are then changed, which modifies the ongoing operation of the sensory prosthesis 110. In some examples, scene-specific sensory prosthesis settings 146 are changed. For instance, the sensory prosthesis settings 146 associated with a speech mode (e.g., as determined by a scene classifier of the sensory prosthesis 110) are changed but not in other modes (e.g., music or wind modes). This scene-specific approach can be advantageous because changes that improve the capability of the sensory prosthesis 110 to produce sensory percepts understandable by a recipient with respect to one kind of sensory events 10 can have a concomitant detrimental effect on the capability of the sensory prosthesis 110 to produce percepts understandable by the recipient relating to other sensory events 10.

In some examples, operation 250 includes operation 254. Operation 254 includes reporting a performance quality of the sensory prosthesis 110 with respect to the sensory event 10. The performance quality can include whether or not the recipient responded appropriately to the sensory event 10, which can be used as a proxy indication of whether the sensory prosthesis 110 accurately caused a sensory percept.

In some examples, operation 250 includes operation 256. Operation 256 includes recommending corrective actions. In an example, the treatment action 251 includes recommending corrective actions for increasing the likelihood of the recipient responding appropriately to sensory events 10. In an example, the corrective action can be a reconfiguration or reprogramming of the sensory prosthesis 110. In another examples, the corrective action is includes modifying therapy provided to the recipient. For instance, where the sensory prosthesis 110 is a unilateral auditory prosthesis, modifying therapy can include advancing to a bilateral prostheses.

In some examples, operation 250 includes operation 258. Operation 258 includes providing a metric estimating the recipient's ability to engage with the sensory event 10. The metrics can include, for example, a total number of appropriate responses 20 to sensory events 10, a total number of inappropriate responses 20 to sensory events 10, a total number of responses 20 per day, a rate of inappropriate responses 20, and an average grade of responses 20. Additionally, trends in such metrics can be computed. The trends can reveal useful information in the sensory health of the recipient, such as determining improvement or decline in the recipient's ability to respond to sensory events 10. Such trend information can be useful in the determining of treatment options for the recipient. Metrics may be segmented based on qualities of the sensory events (if such qualities are detected or known). For example, where the sensory events 10 are musical events, the qualities can include dominant frequencies, tempo, volume, genre, vocalist (e.g., male vocalist, female vocalist, age, languages spoken, accent, etc.). The segmentation of the sensory events 10 based on qualities can further enhance the treatment actions by allowing conclusions to be drawn on the basis of how the recipient is able to perceive specific kinds of sensory events. For example, the metrics can indicate that the recipient is better able to perceive speech in a one-on-one setting rather than in a classroom.

Following operation 250, the flow can return to operation 210.

Example Process—Second Example Process

FIG. 3 illustrates an example process 300 for monitoring an individual's sensory capabilities and taking a treatment action based thereon. As illustrated, the process 300 includes some of the same operations as process 200. Generally the process 300 further includes details regarding the operation of the sensory prosthesis 110 in a monitored mode 30 or an unmonitored mode 40 and further providing an analysis to a caregiver device. In an example, the process 300 begins with operation 310.

Operation 310 includes selectively operating the sensory prosthesis 110 in the monitored mode 30 or the unmonitored mode 40. The monitored mode 30 can be characterized by the sensory prosthesis 110 monitoring for sensory events 10 and monitoring for responses 20 by the recipient. The unmonitored mode 40 can be characterized by the sensory prosthesis 110 not monitoring for sensory events 10 or not monitoring for responses 20 by the recipient. The sensory prosthesis 110 can selectively operate in the modes 30, 40 based on various conditions. In an example, the modes 30, 40 can be manually switched by the recipient or a caregiver.

In some examples, operation 310 includes operation 312. Operation 312 includes operating in the unmonitored mode 40 based on proximity. The proximity can be a proximity between the recipient and a caregiver. It can be advantageous to operate in the unmonitored mode 40 while the recipient is close to a caregiver because, the caregiver can personally monitor how well the recipient is responding to sensory events 10. In such situations, the responses 20 may need not be automatically monitored by the sensory prosthesis 110. By contrast, the caregiver may prefer to have the responses 20 monitored when the recipient is away from the caregiver (e.g., while at school). By selectively operating in the modes 30, 40 (e.g., based on proximity), the sensory prosthesis 110 can conserve computing resources and privacy by avoiding collecting and processing unnecessary data.

In other examples, the proximity can be a proximity between the recipient and another person or location. The proximity can be between a recipient and particular areas of interest. For instance, the recipient can test new settings for the sensory prosthesis 110 to improve the ability of the sensory prosthesis 110 to cause sensory percepts in areas having high levels of noise (e.g., background noise in the case of the sensory prosthesis 110 being an auditory prosthesis). To facilitate data gathering for the testing, the areas of interest can be set (e.g., by a recipient, caregiver, or clinician) to areas likely to have high levels of noise.

The proximity can be determined or inferred in various ways. In an examples the proximity is determined based on user input (e.g., receiving user input indicating that the recipient is proximate the area of interest). In another example, the proximity is determined based on a proximity between the sensory prosthesis 110 and another device, such as a caregiver device (e.g., the computing device 150) as determined based on, for example, nearby wireless signals. In a further example, the proximity is determined based on a location of the sensory prosthesis 110 (e.g., as determined based on satellite-based location data or nearby wireless signals).

In some examples, operation 310 includes operation 314. Operation 314 includes operating in the unmonitored mode 40 based on time. For example, the time can be a current time of day. The recipient, caregiver, or clinician can set one or more time ranges during which to operate in the modes 30, 40. For instance, where the recipient is a child, it may be advantageous to monitor responses 20 to sensory events 10 in the morning when the child is more likely to be alert. This can improve the ability to monitor data to ensure the missed responses 20 are due to operation of the sensory prosthesis 110 rather than the recipient being tired.

Following operation 310, the flow can move to operation 320. Operation 320 can include determining whether the sensory prosthesis 110 is operating in the monitored mode 30 or in the unmonitored mode 40. Responsive to the sensory prosthesis 110 operating in the unmonitored mode 40, the flow can move to operation 330.

Operation 330 includes refraining from detecting occurrences of sensory events 10 proximate the sensory prosthesis. Operation 330 can take various forms. This can include refraining from obtaining event sensor data 212, refraining from processing event sensor data 212, or refraining from taking an action after processing event sensor data 212. In other examples, the operation 330 can include refraining from obtaining response sensor data 231, refraining from processing response sensor data 231, or refraining from taking an action after processing response sensor data 231. Advantageously, the refraining from detecting can conserve battery life of the sensory prosthesis 110 (where the sensory prosthesis 110 is battery powered) and can conserve computing resources. In examples, operation 330 can be performed while in the unmonitored mode 40. Following operation 330, the flow can return to operation 310.

Responsive to operation in the monitored mode 30, the flow can move to operation 210 (e.g., while operating in the monitored mode 30, the flow can move to operation 210), operation 220, operation 230, and operation 240. Operations 210, 220, 230, and 240 can be as described above regarding FIG. 2. Following operation 240, the flow can move to operation 340.

Operation 340 includes storing sensory event data 342 regarding the sensory event 10 and response data 344 regarding the response 20 by the recipient. In some examples, the sensory event data 342 can include the event sensor data 212 and the response data 344 can include the response sensor data 231. In other, examples, the sensory event data 342 is data regarding the determined sensory event 10 (e.g., characterized event sensor data 212) and the response sensor data 231 can include characterized response data 231. For example, the data 342, 344 can include metrics (e.g., as discussed above) regarding the sensory event 10 and the response 20, respectively.

In an example, storing the data 342, 344 can include storing the data 342, 344 as part of an analysis 362 of the sensory event 10 and the response 20. In examples, the operation 340 includes generating the analysis 362.

The data collected and processed regarding the sensory event 10 and the response 20 associated data can be aggregated on the sensory prosthesis 110, the computing device 150 associated with the recipient (e.g., a mobile phone), on the server 170, at another device, or combinations thereof and used to form the analysis 262 of the recipient's ability to perceive or respond to sensory events 10. In examples, the analysis 262 is data that represents conclusions or inferences generated based on the data regarding the sensory event 10 and the response 20. The analysis 262 can be generated based on a comparison of the responses 20 over time, such as how the recipient's responses 20 have changed over time.

In an example, the analysis 262 is generated using decision trees or decision rules describing inferences or conclusions to be drawn based on data. For instance, a decision rule may specify that responsive to a response 20 indicating that the recipient did not perceive a sensory event 10 having particular characteristics, include in the analysis 262 that the recipient has difficulty perceiving sensory events 10 having those characteristics. The analysis 262 can further include the previously-described metrics. Following operation 340, the flow can move to operation 350.

Operation 350 includes transitioning to the unmonitored mode 40. The transitioning can be based on, for example, a user manually transitioning from the unmonitored mode 40 to the monitored mode 30 (e.g., via user input). The transitioning can be performed using or based on one or more of the techniques described above in relation to operation 310. For instance, responsive to the sensory prosthesis 110 coming into proximity with a caregiver device, the sensory prosthesis 110 can automatically transition from the monitored mode 30 to the unmonitored mode. Following operation 350, the flow can move to operation 360.

Operation 360 includes transmitting the analysis 362 based on the sensory event data 342 to a caregiver device. In some examples, operation 360 is performed responsive to transitioning from the monitored mode 30 to the unmonitored mode 40. The analysis 362 can be transmitted automatically to the caregiver device. The operation 360 can include initiating a data connection with the caregiver device via a wired or wireless connection. Following operation 360, the flow can move to operation 250 as described above.

Following operation 250, the flow can return to operation 310.

Machine-Learning Framework

Figure 4:
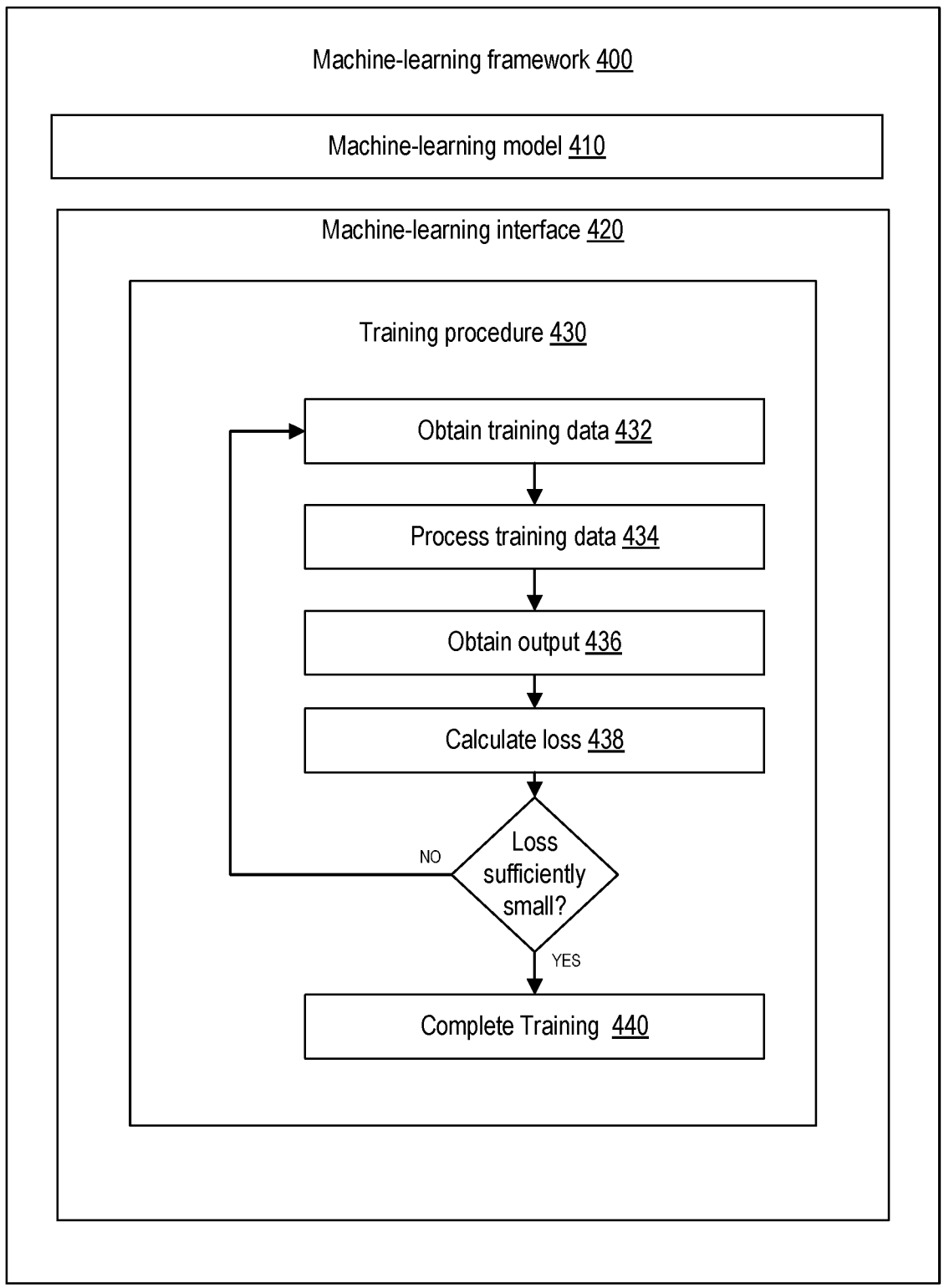
FIG. 4 illustrates an example machine-learning framework that may be used with examples herein.

FIG. 4 illustrates an example machine-learning framework 400 that can be used with examples herein.

The machine-learning framework 400 is software and associated data that implements machine-learning capabilities. In the illustrated example, the machine-learning framework 400 includes two primary components: a machine-learning model 410 and a machine-learning interface 420. One or more aspects of the machine-learning framework 400 may be implemented with machine-learning toolkits, such as: TENSORFLOW by GOOGLE INC. of Mountain View, California; OPENAI GYM by OPENAI of San Francisco, California; or MICROSOFT AZURE MACHINE LEARNING by MICROSOFT CORP. of Redmond, Washington.

The machine-learning model 410 is a structured representation of the learning, such as how learning is achieved and what has been learned. For example, where the machine-learning model 410 includes a neural network, the machine-learning model 410 can define the representation of the neural network (e.g., the nodes of the neural network, the connections between the nodes, the associated weighs, and other data), such as via one or more matrices or other data structures. In another example, where the machine-learning model 410 includes a decision tree, the machine-learning model 410 can define the decision tree (e.g., the nodes of the decision tree and the connections therebetween). The machine-learning model 410 can include multiple different types of machine-learning techniques. For example, the machine-learning model 410 can define multiple different neural networks, decision trees, and other machine-learning techniques and their connections therebetween. For instance, output of a first neural network can flow to the input of a second neural network with the output therefrom flowing into a decision tree to produce a final output.

The machine-learning interface 420 defines a software interface used in conjunction with the machine-learning model 410. For example, the machine-learning interface 420 can define functions, processes, and interfaces for providing input to, receiving output from, training, and maintaining the machine-learning model 410.

In some examples, the machine-learning interface 420 requires the input data to be preprocessed. In other examples, the machine-learning interface 420 can be configured to perform the preprocessing. The preprocessing can include, for example, placing the input data into a particular format for use by the machine-learning model 410. For instance the machine-learning model 410 can be configured to process input data in a vector format and the data provided for processing can be converted into such a format via the preprocessing. In an example, the interface provides functions that convert the provided data into a useful format and then provide the converted data as input into the machine-learning model 410.

The machine-learning interface 420 can define a training procedure 430 for preparing the machine-learning model 410 for use. The machine-learning model 410 can be trained or otherwise configured to receive data (e.g., event sensor data 212 from the sensors 130) as input and provide an output based thereon. For example, the machine-learning model 410 can be trained to receive accelerometer and gyroscope signals as input and provide, as output, an indication whether the signals are indicative of a sensory event 10. The training procedure 430 can begin with operation 432.

Operation 432 includes obtaining training data. The training data is typically a set of human- or machine-curated data having known training input and desired training output usable to train the machine-learning model 410. In examples herein, the training data can include curated event sensor data 212 from many different individuals or artificially-created training data and actual or expected output of the machine-learning model 410 for that data. Following operation 432, the flow can move to operation 434.

Operation 434 includes processing the training data. Processing the training data includes providing the training data as input into the machine-learning model 410. In examples, the training data can be provided as input into the machine-learning model 410 using an associated machine-learning interface 420. Then the machine-learning model 410 processes the input training data to produce an output.

Following operation 434, the flow can move to operation 436. Operation 436 includes obtaining the output from the machine-learning model 410. This can include receiving output from a function. Following operation 436, the flow can move to operation 438.

Operation 438 includes calculating a loss value. A loss function can be used to calculate the loss value, such as based on a comparison between the actual output of the machine-learning model 410 and the expected output (e.g., the training output that corresponds to the training input provided). Attributes of the machine-learning model 410 (e.g., weights of connections in the machine-learning model) are modified based on the loss value, thereby training the model.

If the loss value is not sufficiently small (e.g., does not satisfy a threshold), then the flow can return to operation 432 to further train the machine-learning model 410. This training process continues for an amount of training data until the loss value is sufficiently small. If the loss value is sufficiently small (e.g., less than or equal to a predetermined threshold), the flow can move to operation 440.

Operation 440 includes completing the training. In some examples, completing the training includes providing the machine-learning framework 400 for use in production. For example, the machine learning framework 400 with the trained machine-learning model 410 can be stored on the sensory prosthesis 110, the computing device 150, the server 170, or at another location for use (e.g., for use in detecting a sensory event 10). In some examples, prior to providing the machine-learning framework 400 for use, the trained machine-learning model 410 is validated using validation input-output data (e.g., data having desired outputs corresponding to particular inputs that are different from the training data), and after successful validation, the machine-learning framework 400 is provided for use.

Example Sensory Prostheses

As previously described, the sensory prosthesis 110 can take any of a variety of forms. Examples of these forms are described in more detail in FIGS. 5-8, below. For example, the sensory prosthesis 110 can be an auditory prosthesis, such as a cochlear implant system 510 as described in FIG. 5, a percutaneous bone conduction device 600 as described in FIG. 6, or a transcutaneous bone conduction device 700 as described in FIG. 7. As another example, the sensory prosthesis 110 can be a retinal prosthesis, such as is described in FIG. 8. The sensory prosthesis 110 can take other forms. These different sensory prostheses 110 can benefit from use with the systems and processes described above.

Example Sensory Prostheses—Cochlear Implant System

Figure 5:
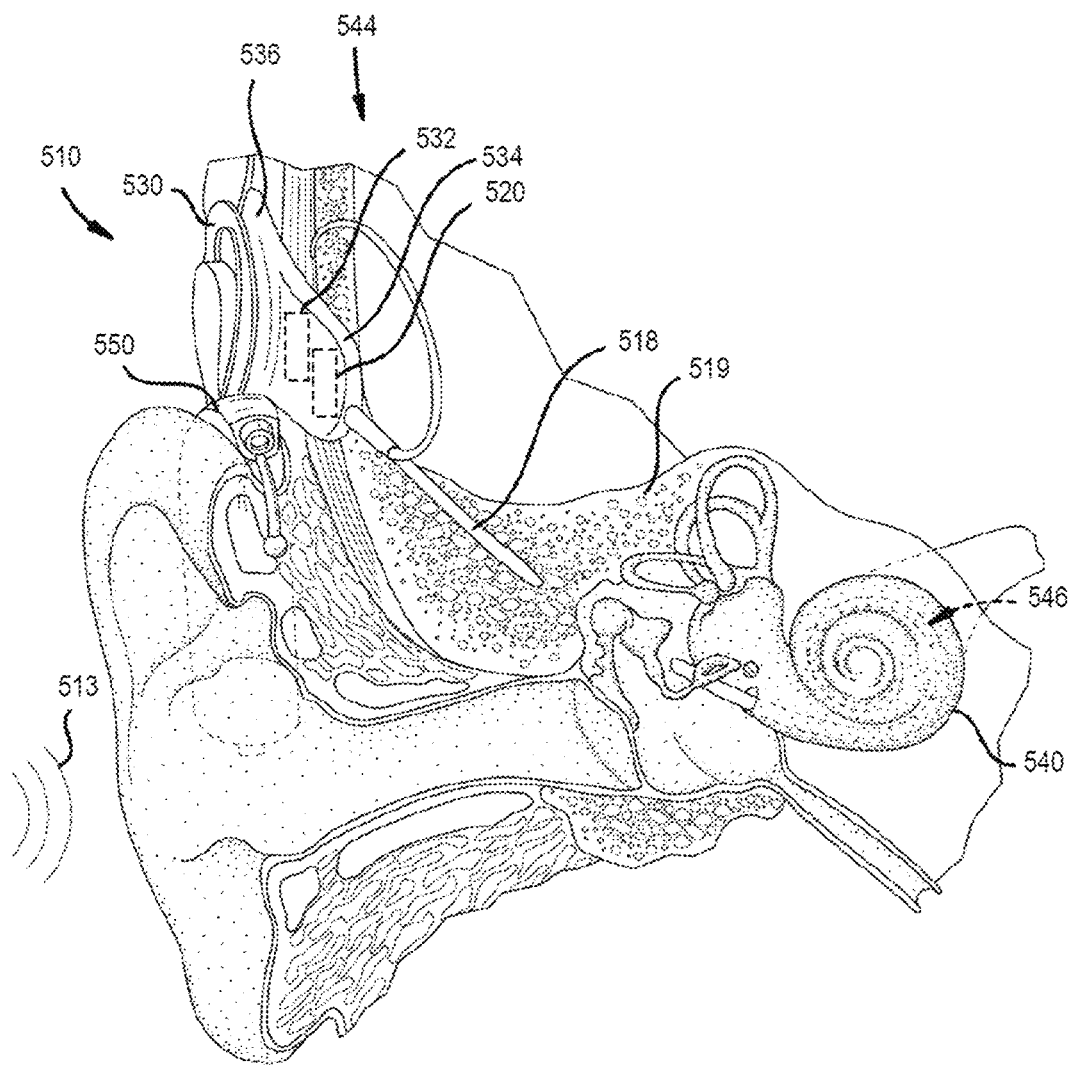
FIG. 5 illustrates an example cochlear implant system that can benefit from use of the examples disclosed herein.

FIG. 5 illustrates an example cochlear implant system 510 that can benefit from use of the technologies disclosed herein. The cochlear implant system 510 includes an implantable component 544 typically having an internal receiver/transceiver unit 532, a stimulator unit 520, and an elongate lead 518. The internal receiver/transceiver unit 532 permits the cochlear implant system 510 to receive signals from and/or transmit signals to an external device 550. The external device 550 can be a button sound processor worn on the head that includes a receiver/transceiver coil 530 and sound processing components. Alternatively, the external device 550 can be just a transmitter/transceiver coil in communication with a behind-the-ear device that includes the sound processing components and microphone.

The implantable component 544 includes an internal coil 536, and preferably, a magnet (not shown) fixed relative to the internal coil 536. The magnet can be embedded in a pliable silicone or other biocompatible encapsulant, along with the internal coil 536. Signals sent generally correspond to external sound 513. The internal receiver/transceiver unit 532 and the stimulator unit 520 are hermetically sealed within a biocompatible housing 534, sometimes collectively referred to as a stimulator/receiver unit 534. Included magnets (not shown) can facilitate the operational alignment of an external coil 530 and the internal coil 536, enabling the internal coil 536 to receive power and stimulation data from the external coil 530. The external coil 530 is contained within an external portion. The elongate lead 518 has a proximal end connected to the stimulator unit 520, and a distal end 546 implanted in a cochlea 540 of the recipient. The elongate lead 518 extends from stimulator unit 520 to the cochlea 540 through a mastoid bone 519 of the recipient. The elongate lead 518 is used to provide electrical stimulation to the cochlea 540 based on the stimulation data. The stimulation data can be created based on the external sound 513 using the sound processing components and based on the sensory prosthesis settings 146.

In certain examples, the external coil 530 transmits electrical signals (e.g., power and stimulation data) to the internal coil 536 via a radio frequency (RF) link. The internal coil 536 is typically a wire antenna coil having multiple turns of electrically insulated single-strand or multi-strand platinum or gold wire. The electrical insulation of the internal coil 536 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Sensory Prostheses—Percutaneous Bone Conduction Device

Figure 6:
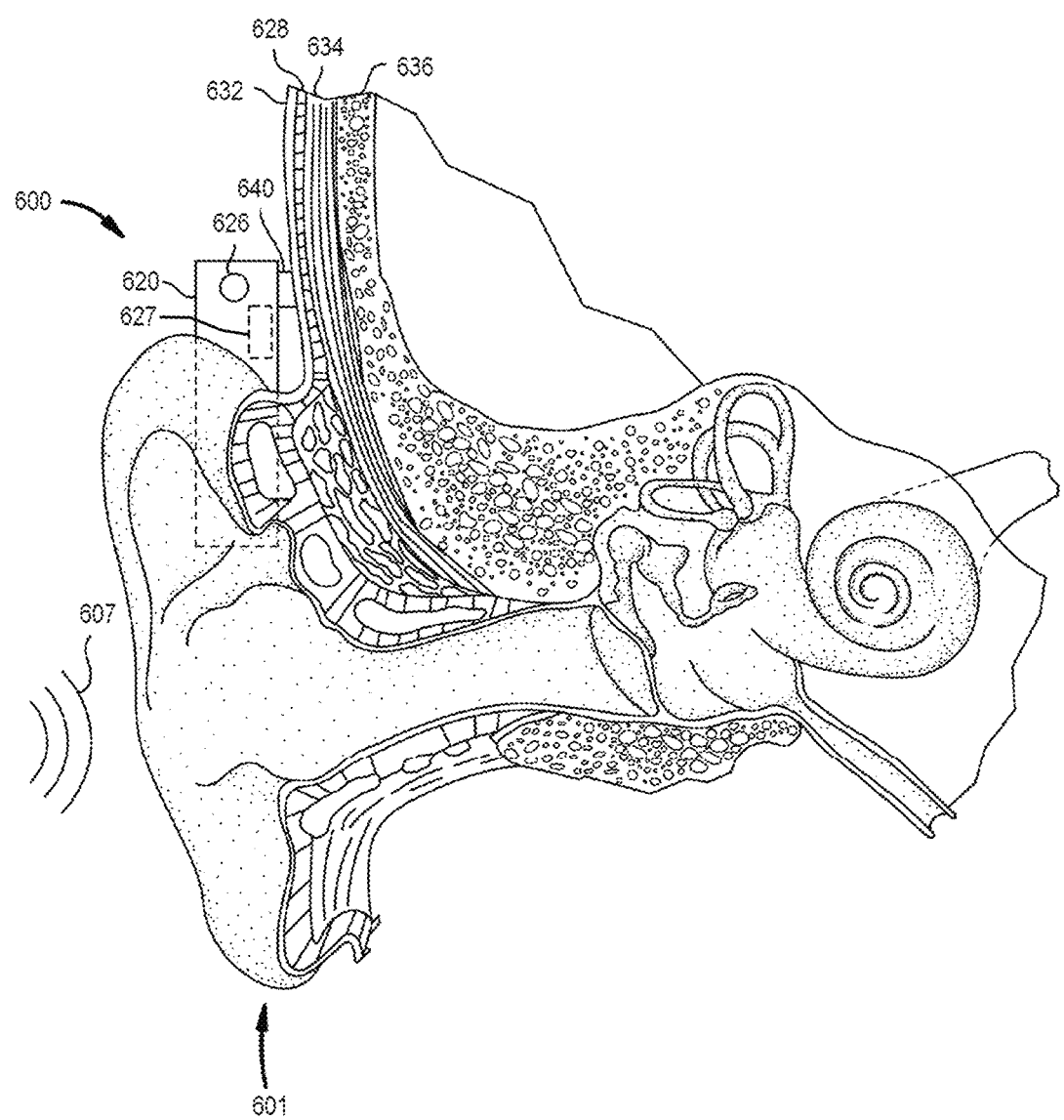
FIG. 6 illustrates an example of a percutaneous bone conduction device that can benefit from use of the examples disclosed herein.

FIG. 6 is a view of an example of a percutaneous bone conduction device 600 that can benefit from use of the technologies disclosed herein. For example, the sensory prosthesis settings 146 of the device 600 can be customized using one or more aspects of disclosed technology. The bone conduction device 600 is positioned behind an outer ear 601 of a recipient of the device. The bone conduction device 600 includes a sound input element 626 to receive sound signals 607. The sound input element 626 can be a microphone, telecoil or similar. In the present example, the sound input element 626 may be located, for example, on or in the bone conduction device 600, or on a cable extending from the bone conduction device 600. Also, the bone conduction device 600 comprises a sound processor (not shown), a vibrating electromagnetic actuator and/or various other operational components.

More particularly, the sound input element 626 converts received sound signals into electrical signals. These electrical signals are processed by the sound processor (not shown). The sound processor generates control signals that cause the actuator 627 to vibrate. In other words, the actuator 627 (also known as the stimulator unit 627) converts the electrical signals into mechanical force to impart vibrations to a skull bone 636 of the recipient. The sound input element 626 and the actuator 627 are placed within a housing 620. The conversion of the electrical signals into mechanical force can be based on the sensory prosthesis settings 146, such that different sensory prosthesis settings 146 may result in different mechanical force being generated from a same sound signal 607.

The bone conduction device 600 further includes a coupling apparatus 640 to attach the bone conduction device 600 to the recipient. In the illustrated example, the coupling apparatus 640 is attached to an anchor system (not shown) implanted in the recipient. An exemplary anchor system (also referred to as a fixation system) may include a percutaneous abutment fixed to the skull bone 636. The abutment extends from the skull bone 636 through muscle 634, fat 628 and skin 632 so that the coupling apparatus 640 may be attached thereto. Such a percutaneous abutment provides an attachment location for the coupling apparatus 640 that facilitates efficient transmission of mechanical force.

Example Sensory Prostheses—Transcutaneous Bone Conduction Device

Figure 7:
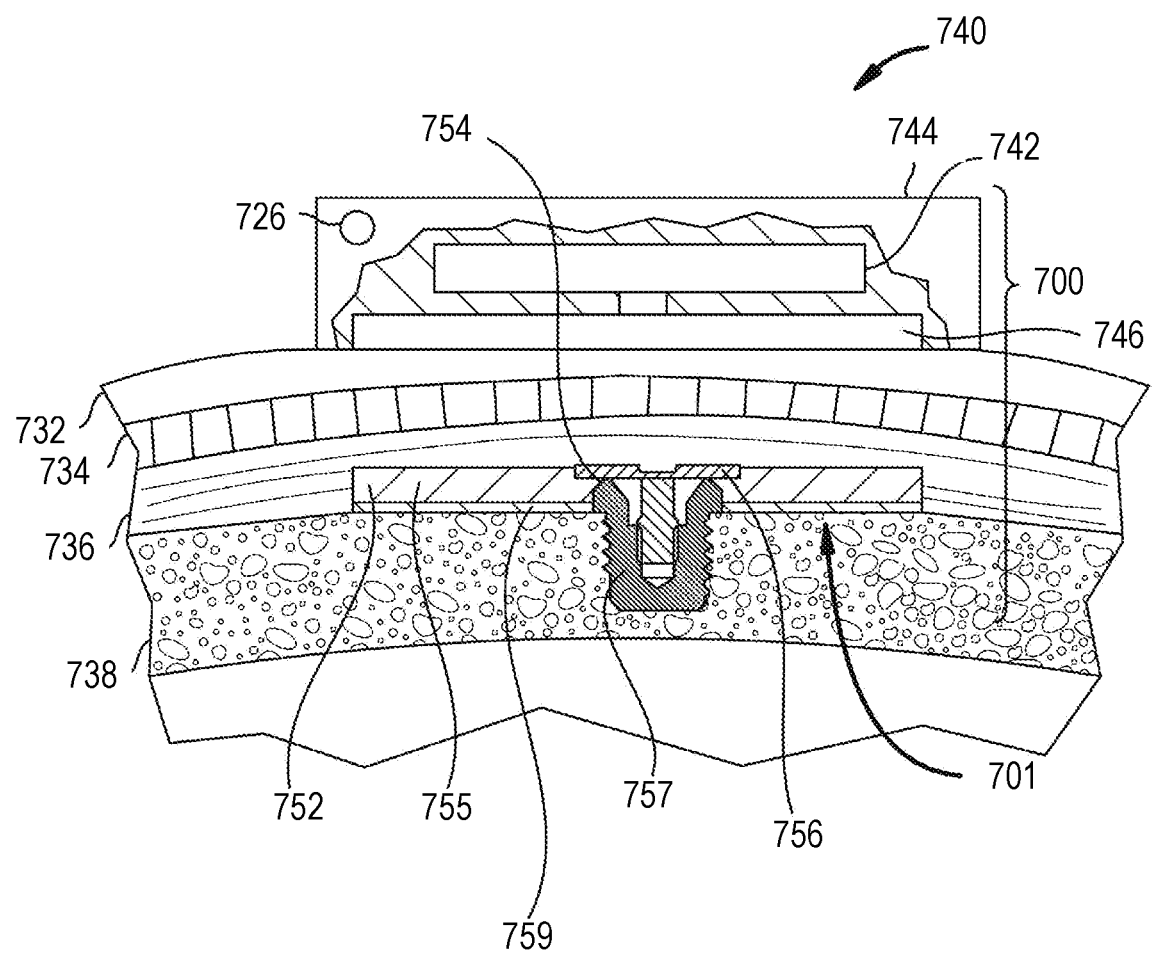
FIG. 7 illustrates an example of a transcutaneous bone conduction device having a passive implantable component that can benefit from use of the examples disclosed herein.

FIG. 7 illustrates an example of a transcutaneous bone conduction device 700 having a passive implantable component 701 that can benefit from use of the technologies disclosed herein. The transcutaneous bone conduction device includes an external device 740 and an implantable component 701. The implantable component 701 includes a passive plate 755 mounted on the bone 738 and is transcutaneously coupled with a vibrating actuator 742 (also known as the stimulator unit 742) located in a housing 744 of the external device 740. The plate 755 may be in the form of a permanent magnet or in another form that generates or is reactive to a magnetic field, or otherwise permits the establishment of magnetic attraction between the external device 740 and the implantable component 750 sufficient to hold the external device 740 against the skin 732 of the recipient.

In an example, the vibrating actuator 742 is a component that converts electrical signals into vibration. In operation, sound input element 726 converts sound into electrical signals. Specifically, the transcutaneous bone conduction device 700 provides these electrical signals to a vibrating actuator 742, or to a sound processor (not shown) that processes the electrical signals, and then provides those processed signals to a vibrating actuator 742. The manner in which the sound processor processes the electrical signals can be modified based on the sensory prosthesis settings 146. The vibrating actuator 742 converts the electrical signals (processed or unprocessed) into vibrations. Because the vibrating actuator 742 is mechanically coupled to a plate 746, the vibrations are transferred from the vibrating actuator 742 to the plate 746. An implanted plate assembly 752 is part of the implantable component 750, and is made of a ferromagnetic material that may be in the form of a permanent magnet, that generates and/or is reactive to a magnetic field, or otherwise permits the establishment of a magnetic attraction between the external device 740 and the implantable component 750 sufficient to hold the external device 740 against the skin 732 of the recipient. Accordingly, vibrations produced by the vibrating actuator 742 of the external device 740 are transferred from plate 746 across the skin 732, fat 734, and muscle 736 to the plate 755 of the plate assembly 752. This may be accomplished as a result of mechanical conduction of the vibrations through the tissue, resulting from the external device 740 being in direct contact with the skin 732 and/or from the magnetic field between the two plates 746, 755. These vibrations are transferred without penetrating the skin 732 with a solid object such as an abutment.

As may be seen, the implanted plate assembly 752 is substantially rigidly attached to a bone fixture 757 in this example. But other bone fixtures may be used instead in this and other examples. In this regard, the implantable plate assembly 752 includes a through hole 754 that is contoured to the outer contours of the bone fixture 757. The through hole 754 thus forms a bone fixture interface section that is contoured to the exposed section of the bone fixture 757. In an example, the sections are sized and dimensioned such that at least a slip fit or an interference fit exists with respect to the sections. A plate screw 756 is used to secure plate assembly 752 to the bone fixture 757. The head of the plate screw 756 can be larger than the hole through the implantable plate assembly 752, and thus the plate screw 756 positively retains the implantable plate assembly 752 to the bone fixture 757. The portions of plate screw 756 that interface with the bone fixture 757 substantially correspond to an abutment screw detailed in greater detail below, thus permitting the plate screw 756 to readily fit into an existing bone fixture used in a percutaneous bone conduction device. In an example, the plate screw 756 is configured so that the same tools and procedures that are used to install and/or remove an abutment screw from the bone fixture 757 can be used to install and/or remove the plate screw 756 from the bone fixture 757. In some examples, there may be a silicone layer 759 disposed between the plate 755 and bone 738.

Example Sensory Prostheses—Retinal Prosthesis

Figure 8:
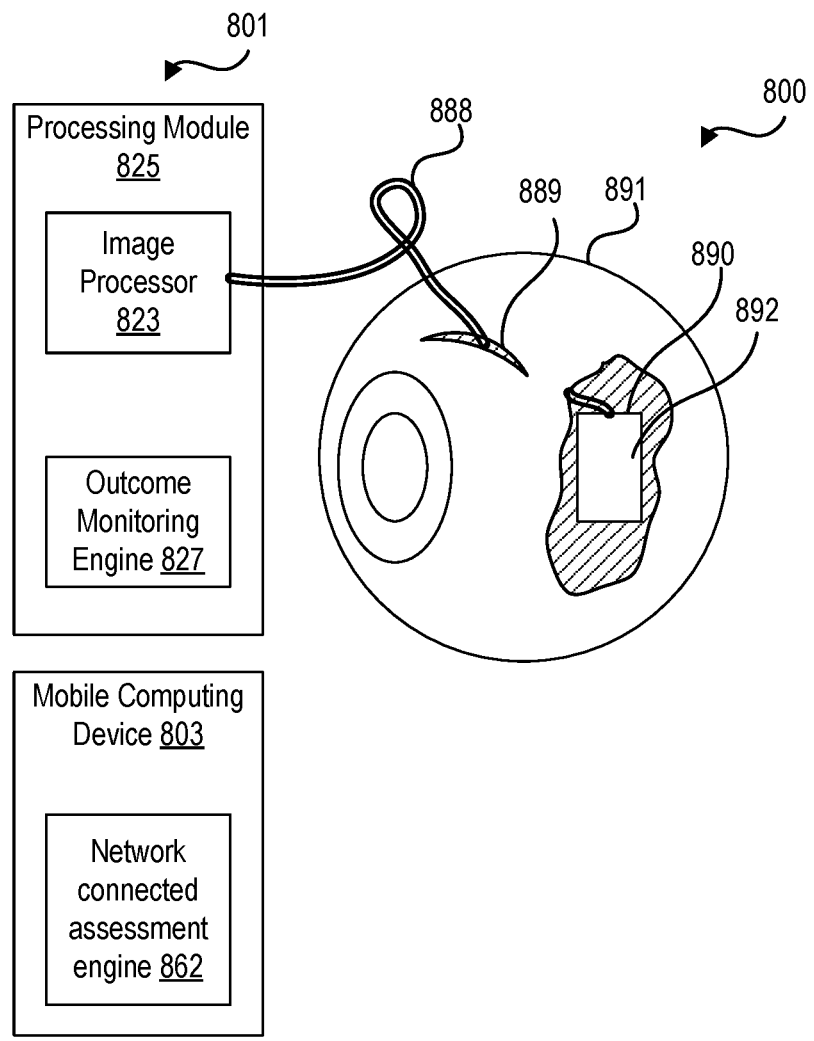
FIG. 8 illustrates an example of a retinal prosthesis system that can benefit from use of the examples disclosed herein.

FIG. 8 illustrates a retinal prosthesis system 801 comprises a retinal prosthesis 800 and a mobile computing device 803. The retinal prosthesis 800 comprises a processing module 825 and a retinal prosthesis sensor-stimulator 890 is positioned proximate the retina 891 of a recipient. In an example, sensory inputs (e.g., photons entering the eye) are absorbed by a microelectronic array of the sensor-stimulator 890 that is hybridized to a glass piece 892 including, for example, an embedded array of microwires. The glass can have a curved surface that conforms to the inner radius of the retina. The sensor-stimulator 890 can include a microelectronic imaging device that can be made of thin silicon containing integrated circuitry that convert the incident photons to an electronic charge.

The processing module 825 includes an image processor 823 that is in signal communication with the sensor-stimulator 890 via, for example, a lead 888 which extends through surgical incision 889 formed in the eye wall. In other examples, processing module 825 may be in wireless communication with the sensor-stimulator 890. The image processor 823 processes the input into the sensor-stimulator 890, and provides control signals back to the sensor-stimulator 890 so the device can provide an output to the optic nerve. That said, in an alternate example, the processing is executed by a component proximate to, or integrated with, the sensor-stimulator 890. The electric charge resulting from the conversion of the incident photons is converted to a proportional amount of electronic current which is input to a nearby retinal cell layer. The cells fire and a signal is sent to the optic nerve, thus inducing a sight perception.

The processing module 825 may be implanted in the recipient or may be part of an external device, such as a Behind-The-Ear (BTE) unit, a pair of eyeglasses, etc. The retinal prosthesis 800 can also include an external light/image capture device (e.g., located in/on a BTE device or a pair of glasses, etc.), while, as noted above, in some examples, the sensor-stimulator 890 captures light/images, which sensor-stimulator is implanted in the recipient.

Similar to the above examples, the retinal prosthesis system 801 may be used in spatial regions that have at least one controllable network connected device associated therewith (e.g., located therein). As such, the processing module 825 includes a performance monitoring engine 827 that is configured to obtain data relating to a "sensory outcome" or "sensory performance" of the recipient of the retinal prosthesis 800 in the spatial region. As used herein, a "sensory outcome" or "sensory performance" of the recipient of a sensory prosthesis, such as retinal prosthesis 800, is an estimate or measure of how effectively stimulation signals delivered to the recipient represent sensor input captured from the ambient environment.

Data representing the performance of the retinal prosthesis 800 in the spatial region is provided to the mobile computing device 803 and analyzed by a network connected device assessment engine 862 in view of the operational capabilities of the at least one controllable network connected device associated with the spatial region. For example, the network connected device assessment engine 862 may determine one or more effects of the controllable network connected device on the sensory outcome of the recipient within the spatial region. The network connected device assessment engine 862 is configured to determine one or more operational changes to the at least one controllable network connected device that are estimated to improve the sensory outcome of the recipient within the spatial region and, accordingly, initiate the one or more operational changes to the at least one controllable network connected device.

Example Computing System

Figure 9:
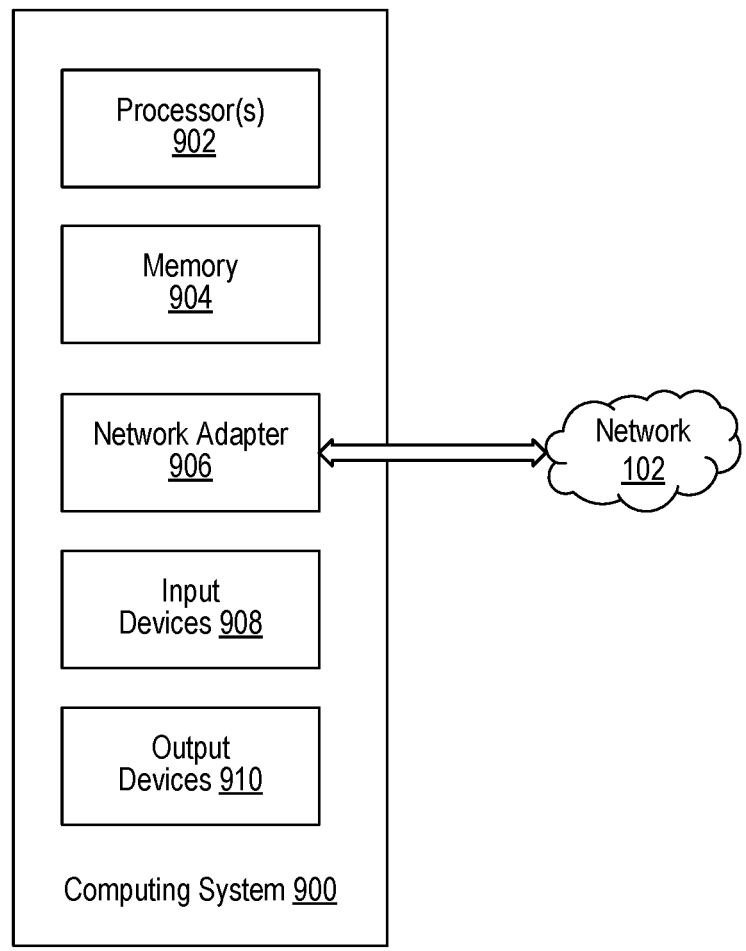
FIG. 9 illustrates an example of a suitable computing system with which one or more of the disclosed examples can be implemented.

FIG. 9 illustrates an example of a suitable computing system 900 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 900 can be a single virtual or physical device operating in a networked environment over communication links to one or more remote devices. The remote device can be a sensory prosthesis (e.g., the sensory prosthesis 110), a personal computer, a server, a router, a network personal computer, a peer device or other common network node. In examples, the computing device 150 and the server 170 includes one or more components or variations of components of the computing system 900. Further, in some examples, the sensory prosthesis 110 includes one or more components of the computing system 900.

In its most basic configuration, computing system 900 includes one or more processors 902 and memory 904.

The one or more processors 902 include one or more hardware or software processors (e.g., Central Processing Units) that can obtain and execute instructions. The one or more processors 902 can communicate with and control the performance of other components of the computing system 900.

The memory 904 is one or more software- or hardware-based computer-readable storage media operable to store information accessible by the one or more processors 902. The memory 904 can store, among other things, instructions executable by the one or more processors 902 to implement applications or cause performance of operations described herein, as well as other data. The memory 904 can be volatile memory (e.g., RAM), non-volatile memory (e.g., ROM), or combinations thereof. The memory 904 can include transitory memory or non-transitory memory. The memory 904 can also include one or more removable or non-removable storage devices. In examples, the memory 904 can include RAM, ROM, EEPROM (Electronically-Erasable Programmable Read-Only Memory), flash memory, optical disc storage, magnetic storage, solid state storage, or any other memory media usable to store information for later access. In examples, the memory 904 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 904 can include wired media such as a wired network or direct-wired connection, and wireless media such as acoustic, RF, infrared and other wireless media or combinations thereof.

In the illustrated example, the system 900 further includes a network adapter 906, one or more input devices 908, and one or more output devices 910. The system 900 can include other components, such as a system bus, component interfaces, a graphics system, a power source (e.g., a battery), among other components.

The network adapter 906 is a component of the computing system 900 that provides network access. The network adapter 906 can provide wired or wireless network access and can support one or more of a variety of communication technologies and protocols, such as ETHERNET, cellular, BLUETOOTH, near-field communication, and RF (Radiofrequency), among others. The network adapter 906 can include one or more antennas and associated components configured for wireless communication according to one or more wireless communication technologies and protocols.

The one or more input devices 908 are devices over which the computing system 900 receives input from a user. The one or more input devices 908 can include physically-actuatable user-interface elements (e.g., buttons, switches, or dials), touch screens, keyboards, mice, pens, and voice input devices, among others input devices.

The one or more output devices 910 are devices by which the computing system 900 is able to provide output to a user. The output devices 910 can include, displays, speakers, and printers, among other output devices.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein. Further, the techniques described herein can be applicable to determining a recipient's response to other stimuli, such as visual stimuli, tactile stimuli, olfactory stimuli, taste stimuli, or another stimuli. Likewise, the devices used herein need not be limited to auditory prostheses and can be other medical devices configured to support a human sense, such as bionic eyes.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A hearing device comprising:
    an implantable or wearable housing;
    a stimulator at least partially disposed within the housing and configured to impart energy to tissue of a recipient of the hearing device to evoke a hearing percept in the recipient;
    a plurality of sensors; and
    a processor configured to:
        receive event sensor data from the plurality of sensors;
        determine an occurrence of an auditory event proximate to the hearing device using the event sensor data;
        determine a vocal response by the recipient to the occurrence of the auditory event using response sensor data;
        characterize the vocal response by the recipient using the response sensor data; and
        initiate a treatment action relating to the recipient based on characterizing the vocal response.

2. The hearing device of claim 1, wherein the plurality of sensors include a microphone, and wherein to determine the occurrence of the auditory event, the processor is configured to:
    receive an audio signal from the microphone;
    determine whether the audio signal includes speech asking a question; and
    responsive to the determining that the audio signal includes the speech asking the question, determine that the auditory event proximate to the hearing device occurred;
    wherein to determine the vocal response by the recipient, the processor is configured to:
        determine a speech response by the recipient; and
    wherein to characterize the vocal response by the recipient, the processor is configured to:
        determine a length of time taken from the question being asked to the recipient beginning to provide the speech response; and
        determine a length of the speech response provided by the recipient.

3. The hearing device of claim 2, wherein to determine the vocal response by the recipient, the processor is configured to:
    determine a behavior of the recipient while the question is being asked.

4. The hearing device of claim 3, wherein to determine the behavior of the recipient, the processor is configured to:
    measure at least one of an amount or duration of stillness of the recipient while the question is being asked.

5. The hearing device of claim 4, wherein to measure at least one of the amount or duration of stillness of the recipient, the processor is configured to:
    measure muscle movement of the recipient using electromyography;
    measure muscle movement of the recipient using a camera;
    measure muscle movement of the recipient using an accelerometer; or
    measure muscle movement of the recipient using a gyroscope.

6. The hearing device of claim 2, wherein to determine the speech response, the processor is configured to:
    determine a vocalization by the recipient using an implanted microphone;
    determine a vocalization by the recipient using an external microphone;
    determine a change in heart rate characteristic of an individual preparing to speak;
    determine an intake of breath characteristic of an individual preparing to speak; or
    determine a cortical cascade of the recipient in response to the question.

7. The hearing device of claim 1, wherein the auditory event includes:
    a sing-song vocal activity;
    a spoken vocal activity;
    a sung vocal activity;
    an onomatopoeia vocal activity;
    a whispered vocal activity; or
    a musical activity.

8. The hearing device of claim 1, wherein the processor is further configured to:
    classify the auditory event as a relevant sensory event or an irrelevant sensory event, wherein detecting the response by the recipient is performed responsive to the auditory event being classified as a relevant sensory event.

9. The hearing device of claim 1, wherein the plurality of sensors include at least one sensor selected from the group consisting of: a microphone, a body noise sensor, a movement sensor, and an implanted electrode sensor.

10. The hearing device of claim 9, wherein the plurality of sensors include the movement sensor; and wherein the movement sensor is an accelerometer or a gyroscope.

11. The hearing device of claim 1, wherein to initiate the treatment action the processor is configured to:
   modify one or more settings of the hearing device;
   report a performance quality of the hearing device with respect to the auditory event;
   recommend corrective actions; or
   provide a metric estimating the recipient's ability to engage with the auditory event.

12. The hearing device of claim 1, wherein the stimulator comprises:
   a stimulator unit disposed within the housing;
   a stimulator assembly disposed at least partially outside of the housing; and
   an array of electrode contacts disposed on the stimulator assembly.

13. The hearing device of claim 1, wherein the processor is configured to cause the hearing device to selectively operate in a monitored mode or an unmonitored mode, and while operating in the monitored mode:
   store auditory event data regarding the auditory event and response data regarding the response by the recipient; and
   responsive to transitioning from the monitored mode to the unmonitored mode, transmit an analysis based on the auditory event data to a caregiver device.

14. The hearing device of claim 13, wherein to selectively operate in the monitored mode or the unmonitored mode includes to:
   operate in the unmonitored mode responsive to a proximity between the hearing device and the caregiver device.

15. The hearing device of claim 13, wherein to selectively operate in the monitored mode or the unmonitored mode includes to:
   operate in the unmonitored mode based on a time of day.

16. The hearing device of claim 13, wherein processor is configured to:
   while in the unmonitored mode, refrain from detecting occurrences of auditory events proximate the hearing device.

17. The hearing device of claim 13, wherein the analysis includes a metric describing an appropriateness of responses to the auditory event.

18. The hearing device of claim 13, wherein to transmit the analysis to the caregiver device includes to:
   directly, automatically, and wirelessly transmitting the analysis from the hearing device to the caregiver device.

19. A method, comprising:
   receiving sensor data from a plurality of sensors proximate a recipient of a hearing device;
   determining an occurrence of an auditory event proximate the hearing device using the sensor data;
   classifying the auditory event as a relevant auditory event or an irrelevant auditory event;
   responsive to the auditory event being a relevant auditory event, detecting a vocal response by the recipient to the occurrence of the auditory event using the response sensor data;
   characterizing the vocal response by the recipient using the response sensor data; and
   initiating a treatment action relating to the recipient based on the characterizing.

20. The method of claim 19, wherein a relevant auditory event is an event expected to elicit a characteristic reaction in the recipient.

21. The method of claim 20, wherein to characterizing the vocal response by the recipient includes:
   determining whether the sensor data is indicative of the recipient performing the characteristic reaction.

22. The method of claim 19, wherein classifying the auditory event as a relevant auditory event or an irrelevant auditory event includes:
   analyzing a location specified by the sensor data.

23. The method of claim 19, wherein classifying the auditory event as a relevant auditory event or an irrelevant auditory event includes:
   comparing a threshold with the sensor data;
   classifying the auditory event as a relevant auditory event responsive to the sensor data satisfying the threshold; and
   classifying the auditory event as an irrelevant auditory event responsive to the sensor data failing to satisfy the threshold.

24. The method of claim 19, further comprising:
   responsive to the auditory event being an irrelevant auditory event, refraining from detecting the vocal response by the recipient to the occurrence of the auditory event.

25. The method of claim 19, further comprising:
   modifying a treatment operation of the hearing device by changing one or more settings of the hearing device.

* * * * *